(12) United States Patent
Labrecque et al.

(10) Patent No.: US 10,842,604 B2
(45) Date of Patent: Nov. 24, 2020

(54) POSITIONING AGENT AND METHOD OF USING THE SAME

(71) Applicant: ATRIUM MEDICAL CORPORATION, Merrimack, NH (US)

(72) Inventors: Roger Labrecque, Londonderry, NH (US); Stephanie Santos, Irvine, CA (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 112 days.

(21) Appl. No.: 16/213,615

(22) Filed: Dec. 7, 2018

(65) Prior Publication Data

US 2019/0175323 A1 Jun. 13, 2019

Related U.S. Application Data

(62) Division of application No. 15/033,134, filed as application No. PCT/US2014/063476 on Oct. 31, 2014, now Pat. No. 10,188,495.

(Continued)

(51) Int. Cl.
*A61F 2/00* (2006.01)
*A61L 31/10* (2006.01)
(Continued)

(52) U.S. Cl.
CPC ........ *A61F 2/0063* (2013.01); *A61L 24/0031* (2013.01); *A61L 27/16* (2013.01);
(Continued)

(58) Field of Classification Search
CPC ...... A61L 27/34; A61L 24/0031; A61L 31/10; A61L 27/16; A61L 27/28; A61L 31/145;
(Continued)

(56) References Cited

U.S. PATENT DOCUMENTS 3,328,259 A 6/1967 Anderson
5,480,436 A 1/1996 Bakker et al.
(Continued)

FOREIGN PATENT DOCUMENTS

JP 2009513182 A 4/2009
JP 2012095769 A 5/2012

OTHER PUBLICATIONS

Official Action issued in counterpart JP Application No. 2016-552256, dated Jun. 11, 2018.
(Continued)

*Primary Examiner* — Phong Son H Dang
(74) *Attorney, Agent, or Firm* — Wesley Scott Ashton

(57) ABSTRACT

A non-setting agent for positioning a surgical mesh prosthesis against a tissue defect during surgical hernia repair enables a surgeon to position the surgical mesh prosthesis at an optimal location against the tissue defect without pre-measuring suture location and pre-suturing. The surgical mesh prosthesis can be repositioned by removing and replacing, or by sliding, the mesh along the tissue defect without traumatizing the tissue. The positioning agent is provided with adhesion and lubricity characteristics providing an adhesion strength required to temporarily maintain the surgical mesh in place, otherwise unsupported, against tissue of a targeted tissue location, and providing a viscosity that permits removal and replacement, or slidable movement, of the surgical mesh along the tissue upon receipt of a non-gravitational external force applied to the surgical mesh so movement of the surgical mesh that is atraumatic to the tissue.

9 Claims, 5 Drawing Sheets

Related U.S. Application Data

(60) Provisional application No. 61/898,764, filed on Nov. 1, 2013.

(51) Int. Cl.
| | |
|---|---|
| *A61L 31/14* | (2006.01) |
| *A61L 24/00* | (2006.01) |
| *A61L 27/16* | (2006.01) |
| *A61L 27/28* | (2006.01) |
| *A61L 27/34* | (2006.01) |
| *A61L 27/50* | (2006.01) |

(52) U.S. Cl.
CPC .............. *A61L 27/28* (2013.01); *A61L 27/34* (2013.01); *A61L 27/50* (2013.01); *A61L 31/10* (2013.01); *A61L 31/145* (2013.01); *A61F 2220/005* (2013.01); *A61F 2220/0008* (2013.01)

(58) Field of Classification Search
CPC .. A61L 27/50; A61F 2/0063; A61F 2220/005; A61F 2220/0008
See application file for complete search history.

(56) References Cited

U.S. PATENT DOCUMENTS

| | | | |
|---|---|---|---|
| 5,634,931 A | 6/1997 | Kugel | |
| 5,899,909 A | 5/1999 | Claren et al. | |
| 6,548,081 B2* | 4/2003 | Sadozai | A61L 31/10 424/426 |
| 6,981,944 B2 | 1/2006 | Jamiolkowski et al. | |
| 7,504,386 B2* | 3/2009 | Pressato | A61P 41/00 514/54 |
| 7,582,576 B2* | 9/2009 | Snijder | A61L 31/048 428/373 |
| 8,124,127 B2 | 2/2012 | Faucher et al. | |
| 10,022,477 B2* | 7/2018 | Kim | A61F 2/0063 |
| 10,188,495 B2* | 1/2019 | Labrecque | A61L 27/16 |
| 2002/0049503 A1* | 4/2002 | Milbocker | C08L 75/04 623/23.72 |
| 2003/0100955 A1* | 5/2003 | Greenawalt | A61L 27/48 623/23.74 |
| 2003/0124087 A1* | 7/2003 | Kim | A61L 31/041 424/78.18 |
| 2005/0054771 A1 | 3/2005 | Sehl et al. | |
| 2006/0078586 A1 | 4/2006 | Ferraro et al. | |
| 2006/0116696 A1* | 6/2006 | Odermatt | A61L 31/10 606/151 |
| 2006/0195010 A1* | 8/2006 | Arnal | A61F 2/0063 600/30 |
| 2007/0077271 A1* | 4/2007 | Dornish | A61L 27/34 424/423 |
| 2007/0202186 A1* | 8/2007 | Yamamoto | A61K 31/722 424/490 |
| 2008/0109017 A1* | 5/2008 | Herweck | A61L 31/16 606/151 |
| 2009/0005867 A1 | 1/2009 | Lefranc et al. | |
| 2009/0017323 A1* | 1/2009 | Webb | C09J 7/29 428/521 |
| 2009/0171377 A1* | 7/2009 | Intoccia | A61F 2/0045 606/151 |
| 2009/0270527 A1* | 10/2009 | Lin | A61K 6/838 523/116 |
| 2011/0038910 A1 | 2/2011 | Faucher et al. | |
| 2011/0087274 A1* | 4/2011 | Sargeant | A61B 17/0057 606/213 |
| 2011/0236460 A1* | 9/2011 | Stopek | A61F 2/0063 424/426 |
| 2011/0276089 A1 | 11/2011 | Straehnz et al. | |
| 2012/0027893 A1* | 2/2012 | Langford | A23K 40/30 426/72 |
| 2012/0209319 A1* | 8/2012 | Bianco-Peled | A61L 24/0094 606/213 |
| 2012/0259348 A1* | 10/2012 | Paul | A61F 2/0063 606/151 |
| 2012/0271290 A1* | 10/2012 | Sargeant | A61B 18/18 606/14 |
| 2013/0071397 A1* | 3/2013 | Schlessinger | A61P 9/10 424/139.1 |
| 2013/0280390 A1* | 10/2013 | Schafer | A22C 13/0003 426/293 |
| 2014/0112972 A1* | 4/2014 | Noishiki | A61L 31/045 424/444 |
| 2014/0257027 A1* | 9/2014 | Palmisano | A61F 2/0063 600/37 |
| 2018/0110897 A1* | 4/2018 | Bush | A61L 24/0031 |

OTHER PUBLICATIONS

Examination Report issued in counterpart Australian Application No. 2014342065, dated Mar. 23, 2018.

Aqualon® Sodium Carboxymethylcellulose, Physical and Chemical Properties, Hercules Incorporated, 1999, Wilmington, Delaware.

Lorenz, Therese, "A Hypothesis for determining the maximum viscosity of sodium carboxymethylcellulose in solutions of divalent cations of high ionic strength" (1996). Thesis. Rochester Institute of Technology, Rochester, New York.

B. Yelimlies et al: "Carboxymethylcellulose coated on visceral face of polypropylene mesh prevents adhesion without impairing wound healing in incisional hernia model in rats" Hernia, vol. 7, No. 3, Sep. 1, 2003, pp. 130-133.

Extended European Search Report for EP14859171.2 (completed Jun. 22, 2017—dated Jun. 30, 2017), which corresponds to this present application.

International Search Report and Written Opinion dated Feb. 11, 2015, issued for corresponding International Application No. PCT/US2014/063476, 11 pages.

Katkhouda, Namir, et al., "Use of Fibrin Sealant for Prosthetic Mesh Fixation in Laparoscopic Extraperitoneal Inguinal Hernia Repair", Advances in Surgical Technique, Annals of Surgery, 2001, vol. 233, No. 1, pp. 18-25.

Katkhouda, Namir, et al., "A new technique for laparoscopic hernia repair using fibrin sealant", Surgical Technology International, vol. 12, pp. 120-126, 2004, Abstract Only (printed from website http://europepmc.org/abstract/MED/15455316/reload=0;jsessionid=DAHpxTMPfBOoJqKWV0zx.24 on Apr. 27, 2016).

International Case Studies, Using Adaptic Touch® Non-Adhering Silicone Dressing: Case Studies, 2013, 14 pages.

Ladurner, R., et al., "Tissue Attachment Strength and Adhesion Formation of Intraabdominal Fixed Meshes with Cyanoacrylat Glues", Eur. J. Med. Res., 2008, vol. 13, pp. 1-7.

Fine, Arthur P., "Laparoscopic Repair of Inguinal Hernia Using Surgisis Mesh and Fibrin Sealant", JSLS, 2006, vol. 10, pp. 461-465.

Melman, Lora, et al., "Evaluation of Acute Fixation Strength for Mechnical Tacking Devices and Fibrin Sealant Versus Polypropylene Suture for Laparoscopic Ventral Hernia Repair", Surgical Innovation, 2010, vol. 17, No. 4, pp. 285-290.

Fridman, Abraham, et al., "Mesh Fixation Devices and Techniques: A Review of the Literature", Bariatric Times, Jun. 12, 2012, vol. 9, No. 6, pp. 10-12 (9 pages in printed PDF form).

Brugger, L., et al., "Objective hypoesthesia and pain after transabdominal preperitoneal hemioplasty: a prospective, randomized study comparing tissue adhesive versus spiral tacks", Surg. Endosc., Apr. 2012, vol. 26, No. 4, pp. 1079-1085, Abstract Only (2 pages in printed PDF form).

Japanese Office Action (with English translation) dated Apr. 22, 2019 for related Japanese patent application No. 2016-552256, 11 pages.

Office Action issued in EP Application No. 14859171.2 dated Mar. 10, 2020, 6 pages.

EP Office Action dated Jun. 25, 2019 during prosecution of EP Patent Application No. 14859171.2, 6 pages.

(56) References Cited

OTHER PUBLICATIONS

EP Office Action dated Feb. 21, 2019 for related EP patent application No. 14859171.2, 6 pages.
Office Action issued in counterpart JP Application No. 2016-552256, dated Jul. 17, 2020, 7 pages.
International Preliminary Report on Patentability issued in counterpart International Application No. PCT/US2014/063476 dated May 3, 2016, 7 pages.
Office Action issued in parent U.S. Appl. No. 15/033,134 dated Dec. 13, 2017, 13 pages.
Anton Paar, Physica MCR, The Modular Rheometer Series, 16 pages, dated Sep. 2004.
Ametek Sensors, Test & Calibration, LTCM Series Motorized Test Stands—LTCM Series from Chatillon, downloaded from http://www.ametektest.com/products/material-testers/motorized-test-stands/ltcm-series on Sep. 13, 2017, 3 pages.
Understanding Absolute and Kinematic Viscosity, downloaded from http://www.machinerylubrication.com/Articles/Print/294 on Sep. 13, 2017, 6 pages.
What is a Rheometer?, downloaded from http://www.innovateus.net/print/science/what-rheometer on Sep. 13, 2017, 3 pages.
Definition of lubricious, downloaded from https://www.merriam-webster.com/dictionary/lubricious on Oct. 11, 2018, 1 page.
Pre-Appeal Examination Report issued in counterpart Japanese Application No. 2016-552256 dated Dec. 23, 2019, 2 pages.

\* cited by examiner

POSITIONING AGENT AND METHOD OF USING THE SAME

This application is a divisional application of U.S. patent application No. 15/033,134 filed on Apr. 29, 2016 (now U.S. Patent 10,188,495, and which claims priority to U.S. Provisional Application no. 61/898,764, which was filed on Nov. 1, 2013, and to International Application no. PCT/US2014/063476, which was filed on Oct. 31, 2014, and which are both incorporated herein by reference in their entirety.

FIELD OF THE DISCLOSURE

This disclosure relates to a substance suitable for positioning a surgical mesh prosthesis against a targeted tissue location of a surgical site, and, more particularly, to a positioning agent that permits a surgical mesh prosthesis to removably adhere in a stationary manner to the targeted tissue location upon placement until permanent fixation of the surgical mesh prosthesis is achieved using a mechanical fixation device, such as sutures, surgical tacks or surgical staples. The positioning agent loaded surgical mesh prosthesis is an implantable device that can be removed and replaced, or easily slid and repositioned, on the targeted tissue upon application of an external force without traumatizing the targeted tissue.

BACKGROUND OF THE DISCLOSURE

Surgical mesh prostheses provide support for organs and other tissues during surgery. Surgical mesh prostheses can be used in a variety of applications, such as urinary incontinence slings, breast supports, chest wall closures, elastomeric device reinforcements, wound dressings, vascular anastomosis reinforcements, but perhaps the most common application of a surgical mesh prosthesis is for use during surgical hernia repair.

A hernia is a protrusion of a tissue, structure, or part of an organ through the muscle tissue or membrane by which it is normally contained. Inguinal hernias are one common type of hernia. In an inguinal hernia, a weakness in the abdominal wall grows into a hole, or defect, that may extend into the inguinal canal of the groin region. Tissue, such as fat or small intestine, protrudes from the defect in the abdominal wall. Other example hernias include ventral hernias, which involve an abnormal outpouching through some portion of the abdominal wall, umbilical hernias, in which intra-abdominal contents protrude through a weakness at the site of passage of the umbilical cord through the abdominal wall, and incisional hernias, which occur in an area of weakness caused by an incompletely-healed surgical wound. Those of skill in the art will appreciate that there are other types of hernias in addition to those specifically mentioned herein.

In order to treat a hernia, such as a ventral hernia or an inguinal hernia, a doctor may insert a specially designed hernia repair mesh prosthesis into an incision near the anatomical defect. Implantable prostheses for repairing anatomical defects in tissue or muscle walls typically are designed to be larger than the defect so as to ensure adequate coverage of the defect and/or sufficient fixation of the prosthesis to tissues surrounding the defect. During implantation, the prosthesis is folded and/or pushed through the surgical incision. In order to allow the prosthesis to be positioned properly, the prosthesis may include positioning straps, portions designed for suturing to the surrounding environment, and/or portions designed for fixation via in-growth of surrounding cells into the prosthesis. Once deployed, the prosthesis unfolds and is maneuvered into a suitable position. The positioned prosthesis is then secured by permanent mechanical fixation. For example, permanent mechanical fixation can include suturing the positioning straps to the margins of the defect, suturing a part of the body of the prosthetic mesh patch to the connective tissue or margins of the defect, and allowing natural in-growth of scar tissue to occur. Excess material, such as excess material on the positioning strap, can be removed before the surgical incision is closed by the surgeon.

In procedures using surgical mesh prostheses, a considerable amount of time is spent measuring and marking both the patient and the mesh prosthesis in an effort to ensure the permanently fixed mesh prosthesis is centered over a defect. For example, in surgical hernia repair, the prosthesis may be pre-sutured prior to inserting it into the abdominal cavity, and the sutures pulled out through the abdominal wall in order to place the surgical mesh prosthesis using the measurements and markings created previously. The combination of these preliminary procedures can add in excess of 30 minutes to the procedural time of the surgical hernia repair.

One approach to minimize the amount of time spent measuring and marking a patient and the surgical prosthetic mesh to ensure proper placement over a tissue defect is to use a mesh prosthesis that contains a self-adhering coating, which is typically applied to the mesh prosthesis prior to sterilization and packaging. However, this approach suffers from several drawbacks. For example, the effectiveness of such coatings can be compromised during the sterilization and packaging processes. In addition, self-adhering coatings comprise synthetic glue, and can cause the surgical mesh to adhere to a tissue defect with such strength that the mesh prosthesis cannot be repositioned to properly cover a tissue defect without first removing the mesh and damaging the tissue adhered to the mesh. Thus, there exists a need for a method of implanting or positioning a surgical mesh against a tissue that minimizes the amount of time spent measuring and marking the patient and mesh while enabling an improperly positioned mesh to be repositioned without damaging the tissue.

SUMMARY OF THE DISCLOSURE

There is a need for a positioning agent having an adhesion strength adequate to maintain a surgical mesh prosthesis temporarily in place, otherwise unsupported, against the tissue of a targeted tissue location during a surgical procedure, and in the absence of setting or curing of the positioning agent. The present invention is directed toward further solutions to address this need, in addition to having other desirable characteristics.

Thus, in accordance with this disclosure, a positioning agent is provided. The positioning agent possesses an adhesion strength adequate to temporarily maintain a surgical mesh prosthesis in place, otherwise unsupported, against tissue of a targeted tissue location during a surgical procedure until the mesh prosthesis is permanently fixated in place against the tissue of to the targeted tissue location using a device for permanent fixation (e.g., sutures, surgical tacks, surgical staples, etc.), wherein the positioning agent exhibits sufficient adhesion strength when applied to the surgical mesh prosthesis to hold it in place against gravity, for example, in the absence of setting or curing of the positioning agent during the implantation procedure.

In accordance with this disclosure, a method of implanting a surgical mesh prosthesis is provided, wherein the method includes the steps of: positioning a surgical mesh prosthesis against a surface of a target tissue with a positioning agent disposed between the surgical mesh prosthesis and the surface of the target tissue, wherein the positioning agent has an adhesion strength adequate to maintain the surgical mesh prosthesis temporarily in place against gravity, otherwise unsupported, against the target tissue in the absence of setting or curing of the positioning agent; wherein the agent is applied to the surface of the target tissue before positioning the surgical mesh prosthesis against the surface of the target tissue and/or wherein the agent is applied to a first side of the surgical mesh prosthesis before positioning the surgical mesh prosthesis against the surface of the target tissue. This method may further include sliding the surgical mesh prosthesis from a first location on the tissue to reposition the surgical mesh prosthesis in a second location on the tissue and/or the method may further include peeling the surgical mesh prosthesis away from a first location on the tissue and placing the surgical mesh prosthesis in a second location on the tissue without traumatizing the tissue. So the positioning agent does not traumatize tissue when the surgical mesh prosthesis is peeled from the tissue or slid on the tissue, the positioning agent is non-setting and has a viscosity suitable to enable slidable movement of the surgical mesh prosthesis along the surface of the target tissue upon application of external force (other than gravity) to the surgical mesh prosthesis and in such a way that the sliding surgical mesh prosthesis is atraumatic to the tissue. Furthermore, the positioning agent has a viscosity under shear that is sufficient to allow for the mesh to slide on the tissue for repositioning, if repositioning is necessary.

In accordance with this disclosure, an implantable device is provided, and a kit that includes components of the implantable device is provided.

BRIEF DESCRIPTION OF THE FIGURES

These and other characteristics of the present invention will be more fully understood by reference to the following detailed description in conjunction with the attached drawings, in which.

DETAILED DESCRIPTION OF ILLUSTRATIVE EMBODIMENTS

Figure 1:
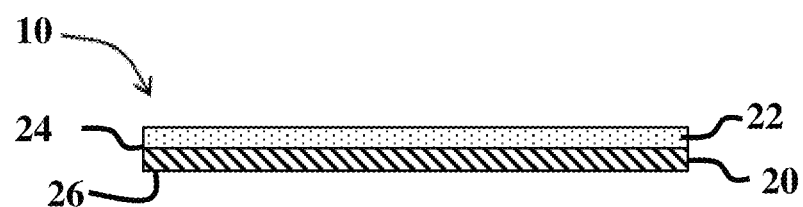
FIG. 1 is a diagrammatic illustration of a positioning agent disposed on a surgical mesh prosthesis according to an embodiment disclosed herein.

An illustrative embodiment of the present disclosure relates broadly to an agent suitable for positioning a surgical mesh prosthesis against a targeted location, and, more particularly, to a positioning agent that permits a surgical mesh prosthesis to removably adhere to a targeted tissue location upon initial placement and to be easily repositioned at an optimal location without traumatizing the tissue to which the surgical mesh prosthesis is attached. For example, the positioning agent may make it possible to slide the mesh prosthesis along the tissue, without having to remove the mesh prosthesis from the tissue, in order to place the mesh prosthesis in the optimal location, wherein the lubricating properties of the positioning agent allow the mesh prosthesis to slide on the tissue without damaging the tissue, or bonding to the tissue. Contrarily, glues and other similar adhesives may create a strong bond with tissue during a surgical procedure, which would prevent a prosthesis from being slid on the tissue surface without abrading, tearing, ripping, severing, shearing, or otherwise damaging the tissue to which it is bonded or over which it slides.

In accordance with this disclosure, a "positioning agent" is a substance that can be used to coat a surgical mesh prosthesis in order to hold the surgical mesh prosthesis in place on the target tissue due to adhesive properties of the substance while permitting the surgical mesh prosthesis to slide on the target tissue without traumatizing the target tissue due to lubrication properties of the substance. Consequently, a positioning agent, in accordance with this disclosure, is a substance that possesses the properties of both a lubricant and an adhesive. The adhesive properties of a positioning agent, in accordance with this disclosure, are those of a non-bonding adhesive, which excludes bonding adhesives that form bonds to the attached surfaces due to evaporation of a solvent or by curing a bonding agent with heat, pressure, or time. Thus, a positioning agent, in accordance with this disclosure, does not form covalent bonds with the tissue of the surgical site during the duration of a surgical procedure (i.e., at least about 30 to 50 minutes), or within about 0 to 30 minutes from application to tissue of a surgical site. Without being limited to a particular theory of adhesion, a positioning agent, in accordance with this disclosure, employs non-bonding adhesion achieved via either van der Waal forces, and/or via dispersion forces, and/or possibly even via hydrogen "bonds," for example. A positioning agent, in accordance with this disclosure, may include some degree of ionic bonding, but it does not include materials that form covalent bonds with the tissue surface during the time frame of a typical surgical procedure (i.e., about 30-50 minutes), or within about 0 to 30 minutes from application to tissue of a surgical site.

Because a positioning agent, in accordance with this disclosure is a non-bonding adhesive with lubricating properties, it is substantially non-setting during the time frame of a typical surgical procedure employing a prosthesis, such as a hernia repair operation (i.e., at least about 30-50 minutes), and excludes bonding adhesives such as aerobic adhesives, anaerobic adhesives, pressure adhesives, light cured adhesives, and covalently chemically bonding adhesives, which form bonds with tissue within the time frame of a typical surgical tissue repair procedure (i.e., at least about 30-50 minutes), or at least not within 0 to 30 minutes from application to tissue. Moreover, because a positioning agent has the properties of both a lubricant and a non-bonding adhesive, it may be characterized as a lubricating non-bonding adhesive.

Suitable materials employable as a lubricating non-bonding adhesive positioning agent are limited only by the lubricating and non-bonding adhesive properties required to permit temporary adhesion with sufficient lubricity to allow sliding movement of the coated surgical mesh prosthesis on the surface of the tissue of the surgical site without causing substantial trauma to the tissue of the surgical site. Furthermore, such suitable materials employable as lubricating non-bonding adhesives must not set, cure and/or bond within the time frame of a typical surgical procedure (i.e., at least about 30-50 minutes), or at least not within at least 0 to 30 minutes from application to tissue at the surgical site, although materials that have a substantially lubricating adhesive phase prior to subsequent change in phase (i.e., hardening, curing, setting) are not necessarily excluded as potential positioning agents. Otherwise, materials suitable for use as a positioning agent include foams, emulsions, waxes, oils, dispersions, slurries, pastes, gels and solutions possessing suitable lubricating and non-bonding adhesive properties. In addition, the positioning agent may contain a solvent, such as may decrease the surface tension of the positioning agent, thereby improving adhesion and/or lubricating properties due to a modification of surface energy. However, the positioning agent does not set upon evaporation of the solvent during the time frame of a typical surgical operation (i.e., at least about 30-50 minutes), as such evaporation induced setting or curing is a characteristic of certain bonding adhesives. In accordance with this disclosure, a positioning agent may comprise a polymer so long as the polymer does not covalently bond to the tissue of the surgical site during the time frame of a typical surgical operation (i.e., at least about 30-50 minutes). In other words, a positioning agent in accordance with this disclosure does not cure or set within the time frame of a typical surgical operation (i.e., at least about 30-50 minutes), or at least not within at least 0 to 30 minutes following application to tissue, wherein curing or bonding are defined as processes in which covalent bonding occurs between molecules of a formulation, and/or in which covalent bonding occurs with tissue, within the about 30-50 minute window of a typical surgical procedure.

In accordance with this disclosure, the positioning agent may constitute a Newtonian fluid or a non-Newtonian fluid. It may be shear thinning or it may be shear thickening. Furthermore, the positioning agent may be homogeneous or non-homogeneous in composition or structure. The positioning agent may be hydrophobic or it may be hydrophilic. In accordance with some embodiments, the positioning agent further comprises a therapeutic agent.

Implantable Surgical Mesh Prosthesis Embodiments

FIGS. 1 through 6, wherein like parts are designated by like reference numerals throughout, illustrate embodiments of an implantable surgical mesh prosthesis 20 coated with a positioning agent 22, and related methods of implanting a surgical mesh prosthesis 20 so as to properly position the surgical mesh prosthesis against tissue 28 at a targeted tissue location 30, according to the present disclosure. Although the present disclosure employs reference to the figures, it should be understood that many alternative forms can embody the subject matter of this disclosure, which is not limited by the figures.

A positioning agent 22, in accordance with this disclosure, has an adhesion strength adequate to maintain an implantable prosthesis (e.g., a surgical mesh prosthesis 20) temporarily in place, otherwise unsupported, against tissue 28 of a targeted tissue location 30, such as a surgical site. It should be appreciated that the positioning agents 22 exhibit the required adhesion strength when coated or applied onto an implantable prosthesis, and in the absence of setting or curing of the positioning agent 22 during implantation of the implantable prosthesis. It should also be appreciated that the target tissue location of the surgical site is typically a location in which the prosthesis, once placed, is subject to forces of gravity acting on the prosthesis to cause it to move and, absent an appropriate adhesion strength provided by the positioning agent, would fall from the target tissue or alternatively slide out of position, unless held in place or supported by an additional structure, such as the surgeon's hand or a laparoscopic trocar. The positioning agent 22 possesses sufficient lubricity, as reflected by a suitable viscosity, that enables slidable movement of the implantable surgical mesh 20 along the surface of tissue 28 upon application of an external force by the surgeon directly, or via laparoscopic trocar, or via an instrument inserted through a laparoscopic trocar, to the surgical mesh prosthesis 20 so that the slidable movement of the surgical mesh prosthesis is substantially atraumatic to the tissue 28. The adhesion properties of the positioning agent 22 enable the positioning agent 22 to again hold the prosthesis 20 in place after slidably moving to its new position.

Examples of suitable positioning agents include, but are not limited to commercially available medical gels, such as the functional gels listed in Table 5. Other suitable agents would be apparent to the skilled artisan based on Table 5 and the ingredients of the substances listed therein, and the present disclosure as a whole.

It should be appreciated that any potential positioning agent tested in accordance with the conditions described herein, which lacks the requisite adhesion strength to temporarily maintain a surgical mesh prosthesis in place, otherwise unsupported, against a target tissue 28, for example, for a period of time sufficient to allow permanent fixation of the mesh in place against the target tissue 28 utilizing an appropriate fixation device (e.g., sutures, surgical tacks, surgical staples, etc.), is not a suitable positioning agent 22 in accordance with this disclosure. Examples of such agents that are not suitable for use as a positioning agent 22, when tested in accordance with the conditions described herein, include DUODERM® paste (a hydrocolloid paste) from ConvaTec, and 10% solids PLURONIC® F127 (poloxamer 407), and silicone grease. Of course, those skilled in the art will appreciate that under certain conditions such substances may be made suitable for use as positioning agents 22 if modified so as to possess suitable lubricity and suitable non-bonding adhesiveness. For example, the PLURONIC® F127 gel may serve as a positioning agent 22 in accordance with this disclosure by lowering the percentage of solids (e.g., a 7.5% solids formulation at 8,500,000 Cps works as a positioning agent 22). The skilled person with the knowledge contained in the present application can readily distinguish which agents are suitable and which agents are not suitable for use as positioning agents 22, for example, by testing the performance characteristics (e.g., dynamic viscosity and acute fixation strength and force of detachment)

of any particular candidate positioning agent 22, as described in the Examples below.

As described above, the positioning agents 22 according to the present disclosure are non-setting in nature. As used herein, "non-setting" means that the positioning agent 22, when coated onto a surgical mesh prosthesis 20, does not substantially set, or substantially cure, during or after placement of the surgical mesh 20 against a tissue surface, within the time frame of a typical tissue defect repair, namely, at least about 30 minutes to about 50 minutes, or at least not within about 0 to 30 minutes from contact with tissue at a surgical site, to impart the positioning agent 22 with the necessary adhesion strength sufficient to maintain the surgical mesh prosthesis 20 in place, otherwise unsupported, against the tissue surface. In other words, there is no substantial physical transformation (e.g., interlocking due to hardening of adhesive in pores of the surface) or chemical transformation (e.g., covalent bonding) of the positioning agent 22 causing the agent to set during the tissue defect repair procedure in a manner that enables or gives the agent the required adhesion strength to hold the surgical mesh 20 in place against gravity. Consequently, the positioning agent 22 according to this disclosure is not an aerobic adhesive (i.e., an adhesive that causes bonding adherence in the presence of oxygen), and it is not an anaerobic adhesive (i.e., an adhesive that causes bonding adherence in the absence of oxygen). However, to the extent that any of the above bonding substances may be modified to possess the lubricity and adhesive properties of a positioning agent of this disclosure, and so as to not covalently bond to either tissue or to its own molecules within about 0 to 30 minutes from contacting tissue at the surgical site, then such modified substances would constitute a positioning agent in accordance with this disclosure.

Thus, the positioning agents 22 of this disclosure function as intended as lubricating non-bonding adhesives irrespective of the presence or absence of oxygen in the environment during the surgical procedure. Furthermore, the positioning agent 22 of this disclosure is not a pressure adhesive (i.e., an adhesive that requires an extended application of force or pressure in order to effect adherence). The positioning agent 22 is not a light cured adhesive (i.e., an adhesive that requires exposure to a light source, such as UV light, in order to effect adherence). The positioning agent 22 is not an adhesive that sets by a chemical reaction (i.e., an adhesive that causes adherence by a chemical reaction that covalently bonds the adhesive to the surface of the tissue at the surgical site). Thus, the positioning agents 22 do not set at or near ambient temperature or in inert environments within the time frame of a typical tissue defect, e.g., hernia, repair procedure (i.e., at least about 30 minutes to about 50 minutes). Preferably, the positioning agents 22 of this disclosure are completely non-setting in that they do not undergo any substantial setting even following time periods substantially longer than about 50 minutes (e.g., indefinitely).

An agent may be identified as a positioning agent 22, according to this disclosure, as those substances which, in tests, can be successfully applied to a surgical mesh prosthesis 20, so as to removably adhere the surgical mesh prosthesis 20 to the targeted tissue location 30 in a manner so that the coated surgical mesh prosthesis 20 can be readily removed from the targeted tissue location 30 without tearing or otherwise substantially injuring the tissue 28. More preferably, the positioning agents 22 of this disclosure are those that can be removed from, and reapplied to, the tissue 28 repeatedly without substantially losing adhesion strength or damaging the tissue 28. It should be noted that the phrase "without substantially losing adhesion strength," in the present application, is well understood by those of skill in the art to indicate that the positioning agents 22 may experience a minor loss of adhesion strength upon removing and reapplying a surgical mesh prosthesis 20 to tissue 28 repeatedly, although without impacting the ability of surgical mesh prosthesis 20 with positioning agent 22 disposed thereon to be removed and reapplied to the tissue 28 repeatedly and still function to adequately adhere the surgical mesh prosthesis 20 to the tissue 28 in accordance with the present description. As those skilled in the art will appreciate, the amount of such minor loss of adhesion strength with repeated application may vary, for example, depending on the particular positioning agent that is used.

The lubrication properties of the positioning agents 22 are reflected by a dynamic viscosity (also known as shear viscosity) of the positioning agent that 22 permits slideable movement of a surgical mesh prosthesis 20 against a targeted tissue location 30 in a manner that is atraumatic to the tissue 28 upon which the surgical mesh prosthesis 20 slides. The positioning agent 22 should be appropriately viscous to impart adequate lubricity to the agent 22 to enable slideable movement for positioning a positioning agent-coated surgical mesh prosthesis 20 along the surface of tissue 28, but not so viscous that the agent becomes immobilized, or otherwise prevented from sliding along the surface of tissue 28 without traumatizing the tissue 28. Thus, the dynamic viscosity of the positioning agent 22 under shear must be sufficient to allow for the coated surgical mesh prosthesis 20 to slide for repositioning. The dynamic viscosity required to enable such slideable movement of a surgical mesh prosthesis 20 against tissue 28, when tested at $0.1\ S^{-1}$ and 23° C. with an Anton Paar MCR 301 rheometer, is between about 150 Cps and 26,000,000 Cps. The dynamic viscosity required to enable slideable movement of a surgical mesh prosthesis 20 against tissue 28 when tested at $9.77\ S^{-1}$ and 23° C. with an Anton Paar MCR 301 rheometer is between about 50 Cps and 2,530,000 Cps.

In accordance with one example embodiment, the positioning agent 22 has a dynamic viscosity of greater than 150 Cps when tested at $0.1\ S^{-1}$ and 23° C., and in accordance with another example embodiment, the positioning agent 22 has a dynamic viscosity less than 26,000,000 Cps when tested at $0.1\ S^{-1}$ and 23° C. In accordance with another example embodiment, the positioning agent 22 has a preferred dynamic viscosity of greater than 150 Cps and less than 26,000,000 Cps when tested at $0.1\ S^{-1}$ and 23° C. In accordance with one example embodiment, the positioning agent 22 has a dynamic viscosity of greater than 50 Cps when tested at $9.77\ S^{-1}$ and 23° C., and in accordance with another example embodiment, the positioning agent 22 has a dynamic viscosity of less than 2,530,000 Cps when tested at $9.77\ S^{-1}$ and 23° C. In accordance with another example embodiment, the positioning agent 22 has a preferred dynamic viscosity of greater than 50 Cps and less than 2,530,000 Cps when tested at $9.77\ S^{-1}$ and 23° C. Preferably, the positioning agent 22 has a dynamic viscosity that does not irreversibly change, absent an external application of force, temperature differences or moisture absorption, by more than 500% over a duration of between 1 minute and 30 minutes.

The positioning agents 22, according to this disclosure, are made to hold a surgical mesh prosthesis 20 temporarily in place at a targeted tissue location 30 until surgical tacks, surgical staples, sutures, or other fixation devices or methods, can be employed to permanently fixate the surgical mesh prosthesis 20 in place against the tissue 28 of the targeted tissue location 30. The positioning agents 22 of this disclosure do not behave or function as a means to permanently fixate the surgical mesh prosthesis 20 to the tissue 28. Instead, a separate step is required of the surgeon to permanently fixate the surgical mesh prosthesis 20 to the targeted tissue location 30 after the surgical mesh prosthesis 20 is properly positioned. Thus, the role of the positioning agent 22 is that of a temporary adhesive used to hold the surgical mesh prosthesis 20 reliably in place at the targeted tissue location 30 until permanent fixation is achieved by, for example, using a tacker or other surgical device that is distinct from the positioning agent 22.

In other words, the positioning agents 22 of this disclosure do not achieve the kind of permanent mesh fixation achieved by surgical tacks, surgical staples, sutures, or other similar mechanical means, used to fixate the surgical mesh prosthesis 20 to a tissue defect. The positioning agents 22 are not equivalent to these surgical devices used for permanent fixation, and are not intended to replace such surgical devices used for permanent fixation. On the contrary, the positioning agents 22 according to this disclosure only need to provide adequate positioning of the surgical mesh prosthesis 20 for a limited time period that is on the order of a typical tissue defect repair operation. The positioning agents 22 of this disclosure also do not include fibrin glues, cyanoacrylate, or UV cured adhesives, to the extent that these substances provide permanent fixation. However, modified forms of fibrin glues, cyanoacrylates, and/or UV cured adhesives that do not form covalent bonds to either tissue or to their own molecules within about 0-30 minutes of application to a tissue surface may constitute positioning agents within the scope of this disclosure as long as these substances have the lubricity and adhesive properties of a positioning agent, according to this disclosure.

The positioning agent 22 of this disclosure imparts a median tensile strength to a surgical mesh prosthesis 20, which is coated with the positioning agent 22 and adhered in a non-bonding manner to a targeted tissue location 30, of about 0.045 kgf (i.e., about 0.44 N).

The adhesion strength of a positioning agent 22 can also be characterized as a force of detachment required to pull a 1"×1" sample of surgical mesh prosthesis 20, temporarily adhered to a horizontal tissue surface 28 (i.e., bovine intestine) utilizing the positioning agent 22, off of the targeted tissue location 30, as tested by lap shear test using a motorized Chatillon® slide (www.chatillon.com) at a rate of 45 in/min (19 mm/sec). Thus, the force of detachment constitutes a shear strength of the positioning agent. As shown in the bar graph of FIG. 5, positioning agents 22 having an adhesion strength characterized by a force of detachment of no more than about 0.15 lbf are considered to possess an adhesion strength sufficient to permit a 1" by 1" surgical mesh prosthesis 20 to removably adhere to a targeted tissue location 30, for example, throughout the duration of a surgical procedure, such as a laparoscopic hernia repair (duration: 30 to 50 minutes). It is to be understood, however, that such adhesion strength is a representative force measured using a 1" by 1" sized mesh adhered to a tissue substrate (i.e., in this case, bovine intestine), and that the force of detachment required to pull off other size meshes may vary, for example, depending on the size of the mesh, as will be appreciated by those skilled in the art.

Figure 5:
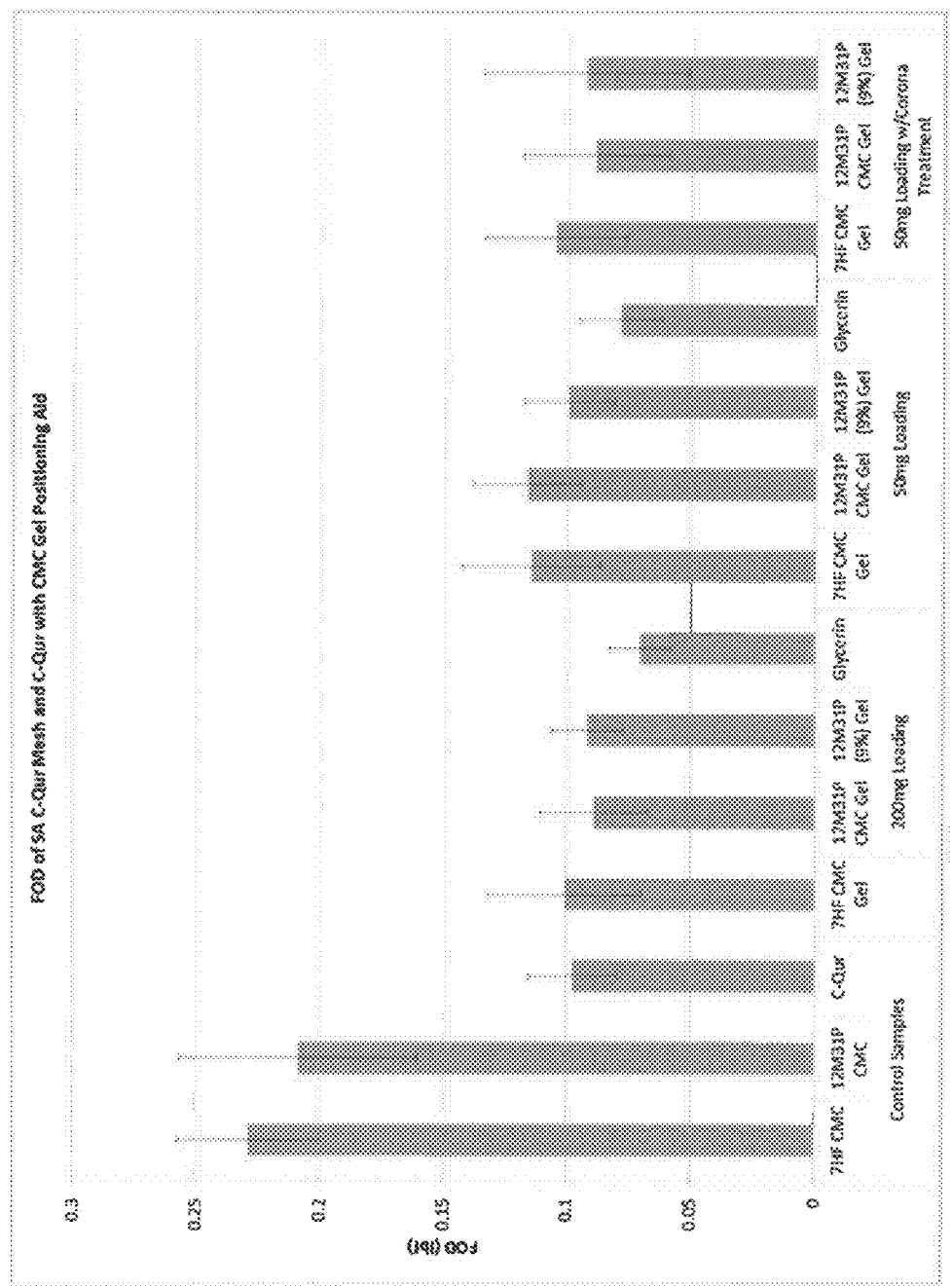
FIG. 5 is a bar graph illustrating the results of force of detachment testing of positioning agents according to embodiments disclosed therein.

From FIG. 5 is should be appreciated that the control samples of C-QUR® mesh (a polypropylene mesh provided with a coating derived from fish oil containing a mixture of trigylcerides and omega 3 fatty acids) coated with pre-dried 7HF CMC and pre-dried 12M31P CMC, respectively, possessed substantially higher adhesive strengths with respect to force of detachment than the other coated mesh samples. For this disclosure, CMC is an abbreviation for sodium carboxymethyl cellulose. However, the adhesive strengths for these two pre-dried control samples did not permit these mesh samples to slide on the bovine intestine substrate because the force of detachment is too high. Consequently, pre-dried 7HF CMC and pre-dried 12M31P CMC are not suitable materials for a positioning agent in accordance with this disclosure.

In addition, uncoated C-QUR® mesh (a polypropylene mesh provided with a coating derived from fish oil containing a mixture of trigylcerides and omega 3 fatty acids) demonstrated a force of detachment substantially similar to the force of detachment of the C-QUR® mesh samples coated with glycerin or CMC containing positioning agents. This is because the force of detachment for the uncoated C-QUR® mesh corresponds to a static force of friction of the uncoated C-QUR® mesh sitting on the unlubricated horizontal bovine intestine tissue surface, while the force of detachment for the positioning agent-coated C-QUR® mesh samples represent the combined forces of the adhesion strengths of the positioning agents and the static force of friction of the positioning agent lubricated surface between the mesh and the horizontal bovine intestinal tissue. Consequently, although uncoated C-QUR® mesh adhered to a horizontal bovine intestine tissue surface due to the force of static friction, it did not adhere to non-horizontal tissue surfaces, such as porcine rib tissue, because the force of gravity pulled the uncoated mesh off the surface of the non-horizontal tissue surfaces. On the other hand, positioning agent-coated C-QUR® mesh, as described below, does adhere to non-horizontal tissue surfaces due to the adhesive strength of the positioning agent. The lap shear test results of FIG. 5, pertaining to the force of detachment of the positioning agent-coated C-QUR® mesh, provides an estimate of the adhesive strength of the positioning agents since the force of static friction of the positioning agent lubricated tissue surface is believed to be substantially lower than the adhesive strength of the positioning agents.

In accordance with an example embodiment, positioning agents 22 having an adhesion strength characterized by a force of detachment of about 0.010 lbf are also expected to possess an adhesion strength sufficient to permit a surgical mesh prosthesis 20 to removably adhere to a targeted tissue location 30, for example, throughout a surgical procedure, such as a laparoscopic hernia repair (duration: 30 to 50 minutes). Thus, a positioning agent 22 according to the present disclosure provides a 1" by 1" sized surgical mesh prosthesis with a force of detachment that ranges from about 0.05 lbf to about 0.15 lbf, which provides sufficient non-bonding adherence of the surgical mesh prosthesis to tissue while also permitting the surgical mesh prosthesis to be slid on the surface of the tissue in view of the dynamic viscosity and shear strength of the positioning agent 22.

Moreover, the positioning agents 22 do not require a surgeon to substantially compress or otherwise hold the surgical mesh prosthesis 20 in place for an extended duration of time in order to achieve adherence of the surgical mesh 20 to the tissue. It should also be understood that the coated surgical mesh prosthesis embodiments and surgical mesh positioning methods of this disclosure are not reliant on a covalent bonding chemistry, and are performed in the absence of an incubation step because the positioning agents 22 of this disclosure are non-polymerizing. The positioning agents 22 may include a polymer as long as it does not react to covalently bond to the tissue 28, or with itself, during the duration of the surgical procedure (i.e., within at least about 0 to 30 minutes following application to a surgical site).

Moreover, the positioning agent 22 of this disclosure is not a mesh fixation material made to prevent migration of a surgical mesh prosthetic 20 by permanently adhering the surgical mesh 20 to the targeted tissue location 30 at the time of the surgical procedure is performed. Thus, the positioning agent 22 according to the present disclosure is generally not a polymerized or a reactive tissue glue, or tissue bonding adhesive material, such as, for example, a synthetic N-butyl-cyanoacrylate glue, or a synthetic material that polymerizes quickly (e.g., on a time scale of seconds to minutes) upon contact with blood or tissue 28. However, if any of these substances are modified so that they possess the same lubricity and adhesive properties as a positioning agent of this disclosure, and also so they do not form covalent bonds with tissue or their own molecules within about 0 to 30 minutes following application to tissue of a surgical site, then such modified polymerized or reactive tissue glues, as well as such modified tissue bonding adhesive materials, would constitute a positioning agent in accordance with this disclosure.

In addition, positioning agents 22 of this disclosure are biocompatible, and preferably do not include substances or components that are toxic to living tissue or carcinogenic, or at least not at levels that are toxic to living tissue or carcinogenic. The positioning agents 22 impart a non-bonding adhesive fixation strength between the surgical mesh prosthesis 20 and the tissue 28 that is less than the fixation strength of a surgical mesh prosthesis 20 fixated to the targeted tissue 28 using a glue or tacker. Thus, the positioning agent 22 of this disclosure is generally not a fibrin sealant, does not comprise substantially only fibrinogen and/or thrombin (i.e., it is not a fibrin or fibrin/thrombin glue), and it does not comprise a biologic adhesive formed by combining a human-derived fibrinogen and calcium chloride-activated thrombin, which, when combined, lead to the formation of polymerized fibrin, such as those that polymerize on a time scale of seconds to minutes. However, if any of these fibrin or fibrin/thrombin glue substances are modified so that they possess the same lubricity and adhesive properties as a positioning agent of this disclosure, and also so they do not form covalent bonds with tissue or their own molecules within about 0 to 30 minutes following application to tissue of a surgical site, then such modified fibrin or fibrin/thrombin glues would constitute a positioning agent in accordance with this disclosure. In accordance with this disclosure, the positioning agents 22 do not polymerize to adhere a surgical mesh prosthesis 20 to a targeted tissue 28 during the time frame of a surgical procedure, and preferably do not comprise a sealant that polymerizes and sets after a period of time, and do not comprise a laminating adhesive.

As used herein "positioning agent" may include a material, substance, or composition that is formulated to facilitate placement of a surgical mesh prosthesis against a tissue surface. Such materials, substances, or compositions, include solutions, gels, foams, emulsions, waxes, oils, dispersions, slurries and pastes, and any combination of these materials Furthermore, the positioning agent 22 may contain a solvent, however, if it does then the solvent does not cause the positioning agent 22 to set upon evaporation of the solvent during the duration of a surgical procedure. Furthermore, the positioning agent 22 may comprise a polymer as long as the polymer does not polymerize to form an adhesive bond with the tissue during the course of the tissue defect repair operation. The skilled artisan will appreciate that, in accordance with this disclosure, it is contemplated that any combination of the above materials can be used as a positioning agent 22.

The present disclosure, and data described herein, demonstrate that, under appropriate conditions as would be apparent to the skilled artisan based upon the teachings and examples described herein, a number of different materials can be used as a positioning agent 22 as long as the material contains the requisite adhesion strength and viscosity, and performs as described herein. In this regard, the present inventors surprisingly and unexpectedly discovered that even different materials, which ordinarily would have apparently opposite and contradictory properties, can function as positioning agents 22 when formulated in accordance with the teachings described herein to possess suitable lubricity and non-bonding adhesive properties. Consequently, the positioning agent 22 can be a Newtonian fluid or a non-Newtonian fluid. It can be shear thinning or shear thickening, homogeneous or non-homogeneous, hydrophobic or hydrophilic.

Figure 2:
FIG. 2 is a diagrammatic illustration of a positioning agent disposed on a tissue according to another embodiment disclosed herein.
Figure 3:
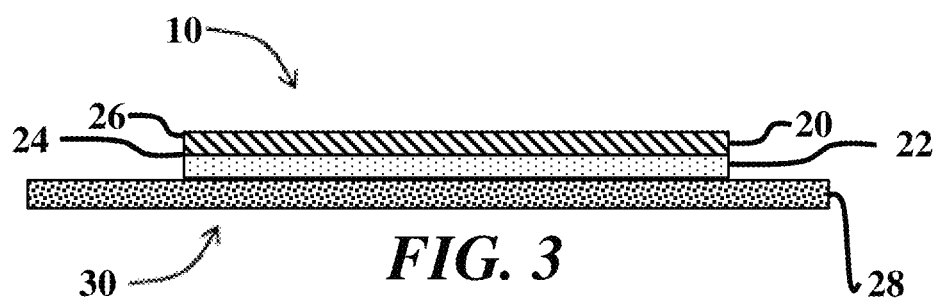
FIG. 3 is a diagrammatic illustration of a positioning agent disposed between a surgical mesh prosthesis and a tissue according to another embodiment disclosed herein.

Those skilled in the art will appreciate that a positioning agent 22 of this disclosure can be applied to, and/or coated on, any suitable implantable prosthetic device 10 (e.g., surgical mesh prosthetic 20) to enable removable adherence of the device 10 against a target tissue location 30, and slidable movement of the device 10 against the targeted tissue location 30. FIG. 1 shows an illustrative non-limiting example embodiment of an implantable device 10. The implantable device 10 includes a surgical mesh prosthesis 20 and a positioning agent 22 disposed on a first side 24 of the surgical mesh prosthesis 20. Although shown as being disposed on the entire surface of the first side 24 of the surgical mesh prosthesis 20, it is to be understood that the positioning agent 22 can be disposed along only a portion of the surface of the first side 24 of the surgical mesh prosthesis 20 to facilitate removable attachment and slideable movement against a targeted tissue 28. Those of skill in the art will also appreciate that instead of, or in addition to, disposing the positioning agent 22 on the first side 24 of the surgical mesh prosthesis 20, the positioning agent 22 can be disposed directly onto tissue 28 of the targeted tissue location 30, as is illustrated in FIG. 2. When the positioning agent 22 is disposed on either the surgical mesh prosthesis 20, the tissue 28, or both the surgical mesh prosthesis 20 and the tissue 28, the surgical mesh prosthesis 20 can be positioned against tissue 28 at a targeted tissue location 30, such that the positioning agent 22 is disposed between the surgical mesh 20 and the tissue 28 at the targeted tissue location 30, as is illustrated in FIG. 3.

Figure 4A:
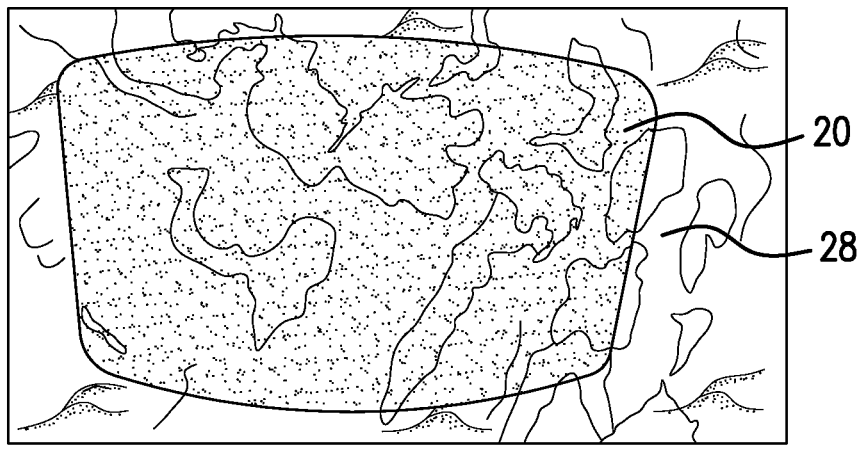
FIG. 4A is a photograph of a positioning agent disposed between a commercially available mesh prosthesis (C-QUR® mesh) and a tissue, viewed upwards (from below) with respect to the mesh prosthesis, according to an embodiment disclosed herein.
Figure 4B:
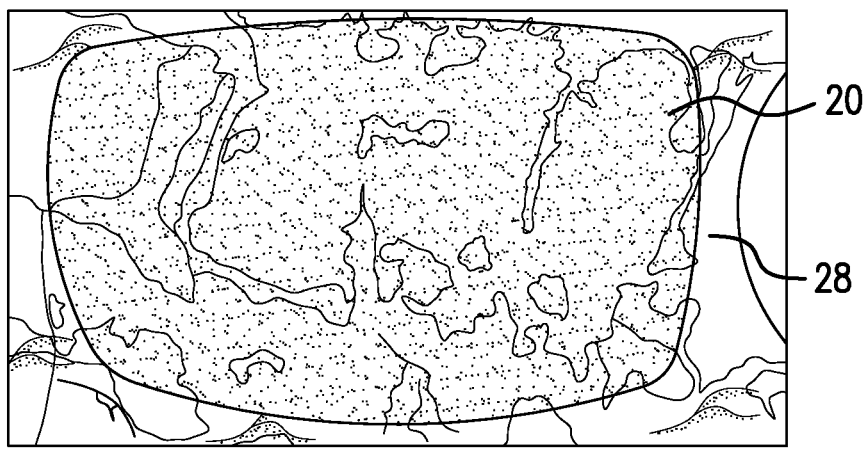
FIG. 4B is a photograph of a positioning agent disposed between a commercially available mesh prosthesis (MOSAIC™ mesh) and a tissue, viewed upwards (from below) with respect to the mesh prosthesis, according to another embodiment of disclosed herein.

FIG. 4A is a photograph showing an exemplary surgical mesh prosthesis 20 (e.g., C-QUR® mesh, which is polypropylene mesh with an Omega 3 gel coating) positioned against a tissue 28 utilizing a positioning agent 22. FIG. 4B is a photograph showing another exemplary surgical mesh prosthesis 20 (e.g., MOSAIC™ mesh, which is an Omega 3 fatty acid (O3FA) coated polypropylene mesh) positioned against a tissue 28 utilizing a positioning agent 22.

Referring back now to FIGS. 1-3, it should also be understood by those of skill in the art that upon application of the positioning agent 22 to the surgical mesh prosthesis 20 or tissue 28, the positioning agent 22 may additionally migrate into any interstitial openings of the surgical mesh prosthesis 20 and occupy uneven surfaces of the tissue 28, thereby providing some degree of non-bonding mechanical adhesion. The first side 24 of the prosthesis 20 can be provided with a rough surface (not shown), for example, to promote tissue ingrowth. The second side 26 of the prosthesis 20 can be provided with a surface, for example, a smooth surface made of a material that functions as an anti-adhesion barrier. For example, the second side 26 of prosthesis 20 can be provided with a non-inflammatory, bioabsorbable, biological oil coating composition to prevent tissue adhesion as is described in U.S. Pat. App. Pub. No. 2006/0078586, and U.S. Pat. No. 8,124,127, which are both incorporated herein by reference in their entirety.

Such non-inflammatory, bioabsorbable, biological oil coating compositions, which form anti-adhesion barriers, can comprise a hydrophobic non-polymeric cross-linked gel, one or more therapeutic agents, and a fatty acid. In a further embodiment, the anti-adhesion barrier coating of second side 26 comprises the hydrophobic non-polymeric cross-linked gel and one or more fatty acids, and further comprises one or more of the group consisting of a glyceride, a glycerol, and a fatty alcohol and also may further comprise a therapeutic agent.

The coating for surface of second side 26 of surgical mesh prosthesis 20 can comprise both soluble and insoluble components. As used in the context of the cross-linked gel coating described herein, the terms "soluble" and "insoluble" refer to the solubility of the coating in a polar solvent such as, e.g., tetrahydrofuran (THF), e.g., as determined by gravimetric analysis. For example, the coatings may be about 60%-75% soluble in THF and about 25%-40% insoluble in THF, or alternatively, the coatings may be about 45-55% soluble in THF and about 45-55% insoluble in THF, or alternatively, the coatings may be about 30%-55% soluble in THF and 45%-70% insoluble in THF, as determined by gravimetric analysis. Generally, at least some of the components resistant to extraction in organic solvent (such as THF) may include cross linked components, which may comprise free or esterified fatty acids with chain lengths of about $C_{10}$-$C_{22}$.

According to this disclosure, the use of any commercially available surgical mesh prosthesis 20 is contemplated that is capable of being rolled up and inserted through a trocar or incision site. Exemplary surgical mesh prosthetics 20, which may be used in the methods disclosed herein, include, but are not limited to, the commercially available hernia surgical mesh prosthetics 20 listed in Table 4 below, except for those commercially available hernia surgical meshes that include a mechanical tissue attachment mechanism that prevents the surgical mesh prosthetic from removably adhering to a targeted tissue 28, or otherwise sliding atraumatically along the tissue 28. Such an exception is the Parietex PROGRIP® mesh, which is a laparoscopic self-fixating mesh including a monofilament polyethylene terephthalate (PET) textile with a large number of polylactic acid microgrips (a mechanical tissue attachment mechanism) and a film composition comprising 70% collagen and 30% glycerol.

In accordance with an example embodiment, positioning agent 22 may be formulated to include a therapeutic agent, for example, to impart a desired biological effect in the targeted tissue location 30 once the surgical mesh prosthetic 20 loaded with the positioning agent 22 is positioned correctly against the targeted tissue 28. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; $10^{th}$ ed. (2006) or 11th edition (July 2009). Suitable therapeutic agents, which can be included in the positioning agent 22 to impart a desired biological effect at a particular targeted tissue location 30, include an antimicrobial agent or composition to minimize or prevent the risk of infection from the surgical procedure, such as an antimicrobial silver composition disclosed in U.S. Pat. App. Pub. No. 2011/0038910, which is incorporated by reference herein in its entirety.

As used herein the terms "antimicrobial," "antimicrobial agent" or "antimicrobial composition" refer to a composition that has the effect of inhibiting the growth of bacteria, fungi, yeast, algae, etc., or killing these micro-organisms. Specific non-limiting examples of antimicrobials include elemental silver, silver nanoparticle, silver nitrate, silver chloride, silver fluoride, silver bromide, silver oxide, silver sulfate, silver carbonate, silver cyanide, silver tetrafluoroborate, silver sulfide, silver acetate, silver lactate, silver benzoate, silver cyclohexanebutyrate, silver diethyldithiocarbamate, silver trifluoromethanesulfonate, triclosan, chlorhexidine, triclocarban, hexachlorophene, dibromopropamidine, chloroxylenol, phenol and cresol. Examples of antimicrobial compounds include, but are not limited to, diamidines, iodine and iodophors, peroxygens, phenols, bisphenols, halophenols, biguanides and silver compounds.

An antibiotic is another example of an antimicrobial agent that may be added to the positioning agent 22. The term "antibiotic" as used herein refers to any compound known to one of ordinary skill in the art to inhibit the growth of, or kill, bacteria. Non-limiting examples of antimicrobial agents that can be used with the biomaterials provided herein, such as the positioning agent 22, include gentamicin sulfate, penicillin g, ephalothin, ampicillin, amoxicillin, augmentin, aztreonam, imipenem, streptomycin, gentamicin, vancomycin, clindamycin, erythromycin, azithromycin, polymyxin, bacitracin, amphotericin, nystatin, rifampicin, tetracycline, doxycycline, chloramphenicol, nalidixic acid, ciprofloxacin, sulfanilamide, gantrisin, trimethoprim, isoniazid, para-aminosalicylic acid, and minocycline.

In one example embodiment, the antimicrobial silver composition that can be included in the positioning agent 22 comprises a silver compound described herein and triclosan (i.e., 2,4,4'-trichloro-2'-hydroxydiphenyl ether). In another example embodiment, the antimicrobial silver composition that can be included in the positioning agent 22 of the present disclosure comprises a silver compound described herein and either chlorhexidine or gentamicin. Other exemplary therapeutic agents and desired biological effects would be apparent to the skilled artisan.

In accordance with one example embodiment, the positioning agent 22 temporarily maintains the surgical mesh 20 in place, otherwise unsupported, against tissue 28 until, for example, the surgical mesh 20 is secured in place against the tissue 28 during a subsequent fixation step. In accordance with one example embodiment, the duration for which the positioning agent 22 maintains the surgical mesh 20 temporarily in place, otherwise unsupported, against the tissue 28 for at least 1 minute. In accordance with one example embodiment, the positioning agent 22 maintains the surgical mesh 20 in place, otherwise unsupported, against tissue 28 for a duration of at least 2 minutes, 3 minutes, 4 minutes, 5 minutes, 6 minutes, 7 minutes, 8 minutes, 9 minutes, 10 minutes, 11 minutes, 12 minutes, or at least 14 minutes. In accordance with one example embodiment, the positioning agent 22 maintains the surgical mesh 20 temporarily in place, otherwise unsupported, against tissue 28 for a duration of at least 15 minutes. In accordance with one example embodiment, the positioning agent 22 maintains the surgical mesh 20 temporarily in place, otherwise unsupported, against tissue 28 for a duration of at least 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, or at least 30 minutes.

In accordance with this disclosure, the positioning agents 22 are not formed by reacting polyeletrophilic components with substituted polyethylene glycol as a polynucleophile, and a polyeletrophilic component composed of a pentaerythritol core with each of the four hydroxyl groups substituted with PEG, and with each PEG branch terminated with a reactive electrophilic group, as described in U.S. Patent Application Publication No. 2005/0054771, which is incorporated herein by reference in its entirety. The positioning agents 22 are also not an adhesive composition comprised of the following components: pentaerythritol polyethylene glycol ether tetra-succinimidyl glutarate, pentaerythritol polyethylene glycol ether tetra-sulfhydryl, and methylated collagen. The positioning agents 22 are also not an adhesive composition comprised of the following components: pentaerythritol polyethylene glycol ether tetra-succinimidyl glutarate, pentaerythritol polyethylene glycol ether tetrasulfhydryl, poly (L-lactic acid) fiber, and methylated collagen.

In accordance with this disclosure, an embodiment of an implantable device is provided, wherein the device includes a surgical mesh prosthesis; and a positioning agent disposed on a first side of the surgical mesh, wherein the positioning agent has an adhesion strength required to maintain the surgical mesh prosthesis temporarily in place, otherwise unsupported, against tissue of a targeted tissue location, wherein the positioning agent exhibits the required adequate adhesion strength in the absence of setting or curing of the positioning agent during implantation of the surgical mesh prosthesis. In accordance with aspects of this embodiment, the positioning agent maintains the surgical mesh temporarily in place, otherwise unsupported, against tissue of the targeted tissue location until the surgical mesh is permanently fixated in place, against tissue of the targeted tissue location utilizing a fixation device. In accordance with this disclosure, a fixation device is not a positioning agent because it effects a permanent fixation and not temporary non-bonding adherence.

In accordance with aspects of this disclosure pertaining to the implantable device, the adhesion strength is characterized by a force of detachment required to pull the device off of the targeted tissue location, wherein this force of detachment may be about 0.10 lbf (about 0.44 N), although this disclosure contemplates a lesser value for the force of detachment so long as the force of detachment is substantially above zero. In accordance with aspects of this disclosure pertaining to the implantable device, the viscosity of the positioning agent under shear is sufficient to allow for the mesh prosthesis to slide for repositioning. Thus, in accordance with aspects of this disclosure pertaining to the implantable device, the positioning agent enables slidable movement of the prosthesis upon application of an external force (i.e., a non-gravitational external force) without abrading the tissue of the targeted tissue location, and/or the positioning agent enables the prosthesis to be peeled away from the targeted tissue location without substantially removing the mesothelium layer from the targeted tissue location.

Thus, in accordance with this disclosure, a first non-limiting embodiment of a positioning agent is provided, wherein the positioning agent includes an adhesion strength required to temporarily maintain a surgical mesh prosthesis in place, otherwise unsupported, against tissue of a targeted tissue location until the mesh prosthesis is permanently fixated in place against tissue of the targeted tissue location, wherein the positioning agent exhibits the adhesion strength when applied to a surgical mesh prosthesis in the absence of setting or curing during implantation. In accordance with a second non-limiting positioning agent of this disclosure, the first non-limiting embodiment is modified so that the positioning agent is a foam. In accordance with a third non-limiting embodiment of the positioning agent, the positioning agent of the first and second embodiments are modified so that the positioning agent is an emulsion. In accordance with a fourth non-limiting embodiment of the positioning agent, the first, second and third non-limiting embodiments are further modified so that the positioning agent is a wax. In accordance with a fifth non-limiting embodiment of the positioning agent, the first, second, third, and fourth non-limiting embodiments are further modified so that the positioning agent is an oil. In accordance with a sixth non-limiting embodiment of the positioning agent, the first, second, third, fourth and fifth non-limiting embodiments are further modified so that the positioning agent is a dispersion. In accordance with a seventh non-limiting embodiment of the positioning agent, the first, second, third, fourth, fifth and sixth non-limiting embodiments are further modified so that the positioning agent is a slurry. In accordance with an eighth non-limiting embodiment of the positioning agent, the first, second, third, fourth, fifth and sixth non-limiting embodiments are further modified so that the positioning agent is a paste.

In accordance with a ninth non-limiting embodiment of the positioning agent, the first, second, third, fourth, fifth, sixth, seventh and eighth non-limiting embodiments are further modified so that the positioning agent contains a solvent. In accordance with a tenth non-limiting embodiment of the positioning agent, the ninth non-limiting embodiment is modified so that the positioning agent does not set upon evaporation of the solvent. In accordance with an eleventh non-limiting embodiment of the positioning agent, the first, second, third, fourth, fifth, sixth, seventh, eighth, ninth and tenth non-limiting embodiments are further modified so that the positioning agent is a gel.

In accordance with a twelfth non-limiting embodiment of the positioning agent, the first, second, fourth, fifth, sixth, seventh, eighth, ninth, tenth and eleventh non-limiting embodiments are further modified so that the positioning agent is a solution. In accordance with a thirteenth non-limiting embodiment of the positioning agent, the first, second, third, fourth, fifth, sixth, seventh, eighth, ninth, tenth, eleventh and twelfth non-limiting embodiments are further modified so that the positioning agent comprises a polymer. In accordance with a fourteenth non-limiting embodiment of the positioning agent, the first, second, third, fourth, fifth, sixth, seventh, eighth, ninth, tenth, eleventh, twelfth, and thirteenth non-limiting embodiments are further modified so that the positioning agent is Newtonian. In accordance with a fifteenth non-limiting embodiment of the positioning agent, the first, second, third, fourth, fifth, sixth, seventh, eighth, ninth, tenth, eleventh, twelfth, thirteenth and fourteenth non-limiting embodiments are further modified so that the positioning agent is non-Newtonian. In accordance with a sixteenth non-limiting embodiment of the positioning agent, the first, second, third, fourth, fifth, sixth, seventh, eighth, ninth, tenth, eleventh, twelfth, thirteenth, fourteenth and fifteenth non-limiting embodiments are further modified so that the positioning agent is shear thinning. In accordance with a seventeenth non-limiting embodiment of the positioning agent, the first, second, third, fourth, fifth, sixth, seventh, eighth, ninth, tenth, eleventh, twelfth, thirteenth, fourteenth, fifteenth and sixteenth non-limiting embodiments are further modified so that the positioning agent is shear thickening.

In accordance with an eighteenth non-limiting embodiment of the positioning agent, the first, second, third, fourth, fifth, sixth, seventh, eighth, ninth, tenth, eleventh, twelfth, thirteenth, fourteenth, fifteenth, sixteenth and seventeenth non-limiting embodiments are further modified so the positioning agent is homogeneous. In accordance with a nineteenth non-limiting embodiment of the positioning agent, the first, second, third, fourth, fifth, sixth, seventh, eighth, ninth, tenth, eleventh, thirteenth, fourteenth, fifteenth, sixteenth, seventeenth, and eighteenth non-limiting embodiments are modified so that the positioning agent is non-homogeneous. In accordance with a twentieth non-limiting embodiment of the positioning agent, the first, second, third, fourth, fifth, sixth, seventh, eighth, ninth, tenth, eleventh, twelfth, thirteenth, fourteenth, fifteenth, sixteenth, seventeenth, eighteenth and nineteenth non-limiting embodiments are modified so that the positioning agent is hydrophobic. In accordance with a twenty-first non-limiting embodiment of the positioning agent, the first, second, third, fourth, fifth, sixth, seventh, eighth, ninth, tenth, eleventh, twelfth, thirteenth, fourteenth, fifteenth, sixteenth, seventeenth, eighteenth and nineteenth non-limiting embodiments are modified so that the positioning agent is hydrophilic. In accordance with a twenty-second non-limiting embodiment of the positioning agent, the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, and twenty-first non-limiting embodiments are modified so that the positioning agent further comprises a therapeutic agent. In accordance with a twenty-third non-limiting embodiment of the positioning agent, the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first and twenty-second non-limiting embodiments are modified so that the positioning agent is non-setting.

Surgical Kit Embodiment

In accordance with one example embodiment, a kit for surgical repair of a tissue defect (e.g., a kit for surgical hernia repair) is provided. The kit can include a surgical mesh prosthesis 20, and a positioning agent 22 in accordance with the detailed description of the current disclosure. In accordance with one example embodiment, the kit further includes a positioning agent applicator (not shown). Furthermore, the positioning agent 22 may be pre-loaded in the positioning agent applicator. In accordance with one example embodiment, the surgical mesh prosthesis 20, the positioning agent 22, and the positioning agent applicator are packaged individually. Furthermore, the positioning agent 22 may be pre-applied to a first side 24 of the surgical mesh prosthesis 20. The kit can also include instructions for applying the positioning agent 22 to the surgical mesh prosthesis 20, as well as instructions for using the positioning agent 22 to implant the surgical mesh prosthesis 20 or to position the surgical mesh prosthesis 20 against a targeted tissue 28.

In accordance with the present disclosure, the positioning agent 22 enables slidable movement of the prosthesis 20 upon application of an external force other than gravity without abrading the tissue 28 of the targeted tissue location 30. The external force can be applied using any means available to the skilled artisan, for example, by using a laparoscopic grasper to grasp the prosthesis 20 and slide the prosthesis 20 into position over a tissue defect, or alternatively by using a surgeon's fingers to grasp and slide the prosthesis 20 into position.

In accordance with the present disclosure, a kit embodiment is provided, wherein the kit includes a surgical mesh prosthesis, and a non-setting positioning agent, wherein the positioning agent has an adhesion strength adequate to maintain the surgical mesh prosthesis temporarily in place, otherwise unsupported, against tissue of a targeted tissue location until the surgical mesh prosthesis is secured permanently in place utilizing a fixation mechanism. In accordance with aspects of this disclosure pertaining to the kit embodiment, the positioning agent may include a viscosity adequate to enable slidable movement of the surgical mesh prosthesis along the tissue upon receipt of external force (i.e., a non-gravitational external force) applied to the surgical mesh prosthesis so that sliding movement of the surgical mesh prosthesis is atraumatic to the tissue. In accordance with aspects of this disclosure pertaining to the kit embodiment, the dynamic viscosity of the positioning agent when tested at 0.1 $S^{-1}$ and 23° C. is between about 150 Cps and about 26,000,000 Cps, and/or the dynamic viscosity when tested at 9.77 $S^{-1}$ and 23° C. is between about 50 Cps and about 2,530,000 Cps.

In accordance with this disclosure, the kit embodiments may further include a positioning agent applicator, wherein the positioning agent may be pre-loaded in the positioning agent applicator, or it may not be pre-loaded in the positioning agent applicator. In accordance with aspects of this disclosure pertaining to the kit embodiments, the surgical mesh prosthesis, the positioning agent, and the positioning agent applicator may be packaged individually, or they may be packed together. In accordance with aspects of the kit embodiment, the positioning agent may be pre-applied to a first side of the surgical mesh prosthesis prior to packaging of the kit.

Thus, in accordance with a first non-limiting kit embodiment of this disclosure, a kit is provided that includes: a surgical mesh prosthesis; and a non-setting positioning agent, wherein the positioning agent has an adhesion strength required to maintain the surgical mesh prosthesis temporarily in place, otherwise unsupported, against tissue of a targeted tissue location until the surgical mesh prosthesis is secured permanently in place utilizing a fixation mechanism. In accordance with a second non-limiting embodiment of the kit, the first non-limiting embodiment of the kit is modified so that the positioning agent further comprises a viscosity required to enable slidable movement of the surgical mesh prosthesis along the tissue upon receipt of non-gravitational external force applied to the surgical mesh prosthesis so that the sliding movement is atraumatic to the tissue. In accordance with a third non-limiting embodiment of the kit, the first and second non-limiting embodiments of the kit are further modified so that the dynamic viscosity of the positioning agent when tested at 0.1 $S^{-1}$ and 23° C. is between about 150 Cps and 26,000,000 Cps. In accordance with a fourth non-limiting embodiment of the kit, the first, second and third non-limiting embodiments of the kit are further modified so that the dynamic viscosity when tested at 9.77 $S^{-1}$ and 23° C. is between about 50 Cps and 2,530,000 Cps.

In accordance with a fifth non-limiting embodiment of the kit, the first and second non-limiting embodiments of the kit are modified to further include a positioning agent applicator. In accordance with a sixth non-limiting embodiment of the kit, the fifth non-limiting embodiment is further modified so that the positioning agent is pre-loaded in the positioning agent applicator. In accordance with a seventh non-limiting embodiment of the kit, the fifth and sixth non-limiting embodiments of the kit are modified so that the surgical mesh prosthesis, the positioning agent, and the positioning agent applicator are packaged individually. In accordance with an eighth non-limiting embodiment of the kit, the first, second, third, fourth, fifth, sixth and seventh non-limiting embodiments are further modified so that the positioning agent is pre-applied to a first side of the surgical mesh prosthesis.

Method Embodiments

Figure 6:
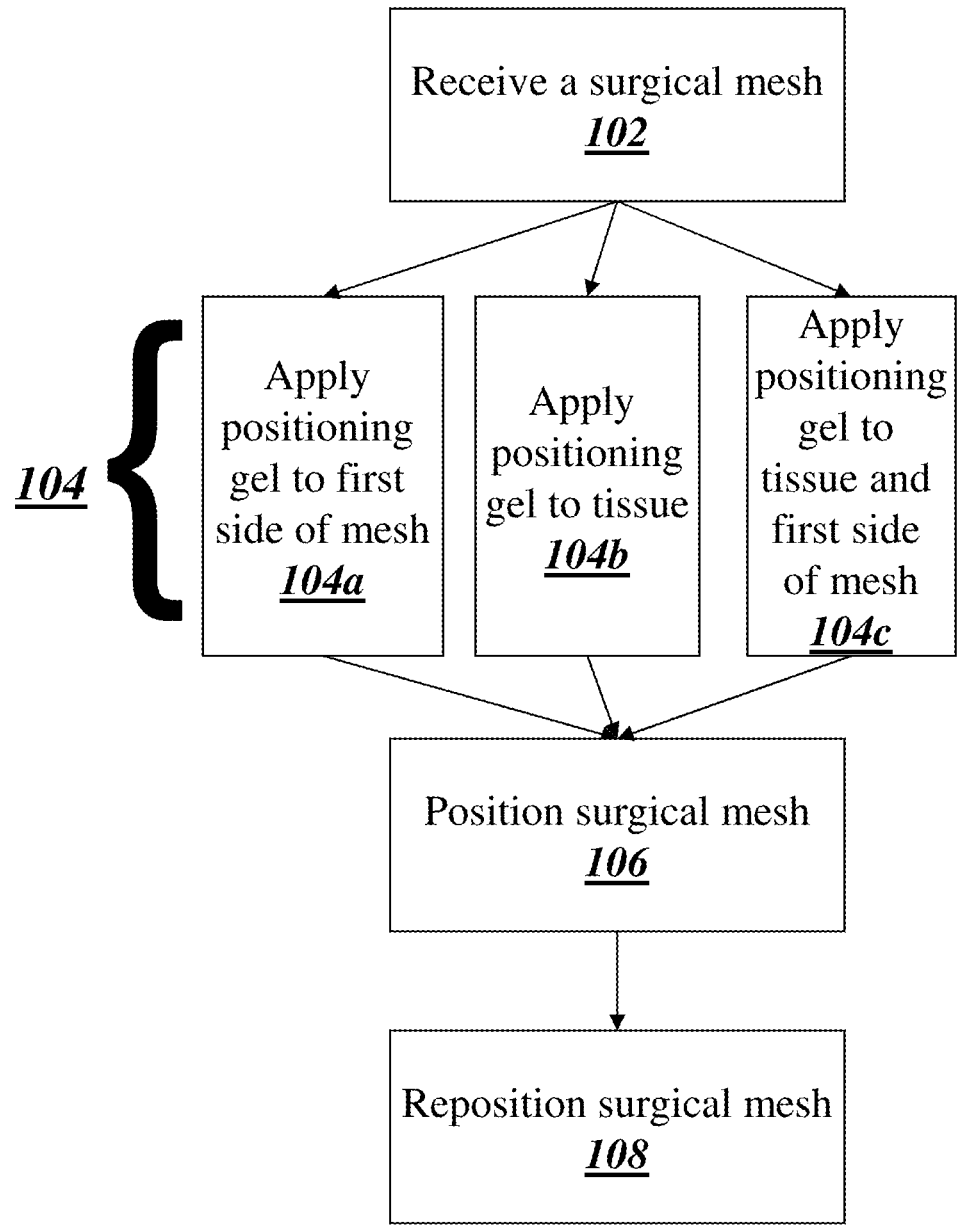
FIG. 6 is a flow chart illustrating an example embodiment of a method of implanting a surgical mesh prosthesis disclosed herein.

FIG. 6 is a flow chart illustrating non-limiting example embodiments of a method of implanting a surgical mesh prosthesis 20. As shown in FIG. 6, the method includes providing a surgical mesh prosthesis 20 (e.g., a previously sterilized surgical mesh 20) (step 102), applying a positioning agent 22 (step 104) in accordance with the detailed description to either a first side 24 of the surgical mesh prosthesis 20 (step 104a), or to tissue 28 at a targeted tissue location 30 (step 104b), or both to the first side 24 of the surgical mesh prosthesis 20 and to the tissue 28 at the targeted tissue location 30 (step 104c), and positioning the surgical mesh prosthesis 20 against a targeted tissue location 30 (step 106). If necessary, the surgical mesh prosthesis 20 can be repositioned (step 108) as often as needed. It should also be appreciated that it may be desirable to clean or moisten the targeted tissue location 30 with a moistening solution before implanting the surgical mesh 20, such as a 0.9% saline solution. Furthermore, following step 108, the surgeon must permanently fix the surgical mesh prosthesis 20 to the tissue at or near the targeted tissue location 30 using a device for permanent fixation, such as surgical staples, surgical tacks, sutures, or other suitable fixation devices.

In accordance with one example embodiment, a method of implanting a surgical mesh prosthesis 20 includes providing a surgical mesh prosthesis 20 (e.g., a previously sterilized surgical mesh prosthesis 20), providing a positioning agent 22 having an adhesion strength adequate to maintain the surgical mesh prosthesis 20 temporarily in place, otherwise unsupported, against the tissue 28 of the targeted tissue location 30, and in the absence of setting or curing of the positioning agent 22; and positioning the surgical mesh prosthesis 20 against the tissue 28 of the targeted tissue location 30 with the positioning agent 22 disposed between the surgical mesh prosthesis 20 and the tissue 28 in such a way that the positioning agent 22 non-bondingly adheres the surgical mesh 20 to the tissue 28 in the absence of setting or curing of the positioning agent 22. In accordance with one example embodiment, the positioning agent 22 is applied to the tissue 28 of the targeted tissue location 30 before positioning the surgical mesh prosthesis 20 against the tissue 28, or the positioning agent 22 is applied to a first side 24 of the surgical mesh prosthesis 20 before positioning the surgical mesh prosthesis 20 against the tissue 28, or the positioning agent 22 is applied to a first side 24 of the surgical mesh prosthesis 20 and to the tissue 28 of the targeted tissue location 30 before positioning the surgical mesh prosthesis 20 against the tissue 28.

The step 104 of applying the positioning agent (e.g., to the first side 24 of the surgical mesh prosthesis 20, or to tissue 28 at the targeted tissue location 30, or to both the first side 24 of the surgical mesh prosthesis 20 and the tissue 28 at the targeted tissue location 30) can be performed in a variety of ways, as will be appreciated by the skilled artisan. For purposes of illustration and not of limitation, however, the following description details various ways of applying the positioning agent 22 to the first side 24 of the surgical mesh prosthesis 20. Such teachings can be readily adapted by the skilled artisan for application of the positioning agent 22 to tissue 28 in lieu of, or in addition to, application of the positioning agent 22 to the first side 24 of the surgical mesh prosthesis 20.

In accordance with one example embodiment, applying the positioning agent 22 to the first side 24 of the surgical mesh prosthesis 20 (step 104a) is performed before the surgical mesh prosthesis 20 is introduced into the patient. In such embodiment, the positioning agent 22 can be applied to at least a portion of the surface of the first side 24 of the surgical mesh prosthesis 20 before the surgical mesh prosthesis 20 is rolled with the first side 24 facing in, grasped, using a laparoscopic grasper, for example, and then inserted through a trocar or incision site to deploy the mesh prosthesis 22 onto the internal abdominal wall with the second side 26 of the surgical mesh prosthesis 20 in contact with abdominal viscera. Of course, the positioning agent 22 can be applied to the entire surface of the first side 24 of the surgical mesh prosthesis 20 before the surgical mesh prosthesis 20 is rolled and introduced into the patient.

In accordance with one example embodiment, applying the positioning agent 22 to the first side 24 of the surgical mesh prosthesis (step 104a) can be performed using an applicator after the surgical mesh prosthesis is inserted into the patient. In such embodiment, the surgical mesh prosthesis 20 is rolled with the first side 24 facing in without first applying a positioning agent 22 to the first side 24 of the surgical mesh 20, grasped, and then the rolled surgical mesh prosthesis 20 can be inserted through a trocar to deploy the surgical mesh prosthesis 20 onto the internal abdominal wall with the second side 26 of the surgical mesh 20 in contact with the abdominal viscera. Next, the applicator is inserted through the trocar or incision site and the positioning agent 22 is applied intra-abdominally to the first side 24 of the surgical mesh prosthesis 20. The present disclosure contemplates the use of any suitable applicator that is capable of loading the surgical mesh prosthesis 20 with an appropriate amount of positioning agent 22 so removable non-bonding adherence of the surgical mesh prosthesis 20 to the targeted tissue location 30 occurs, and so as to enable slidable movement of the surgical mesh prosthesis 20. An example of such an applicator is a tube attached to the end of a syringe loaded with a unit dosage of the positioning agent 22. As will be appreciated by those skilled in the art, the amount of positioning agent 22 required to enable removable attachment to tissue 28 and slideable movement of the surgical mesh prosthesis 20 on tissue 28 may vary, depending on the size of the surgical mesh prosthesis 20 to be implanted, the composition of the agent positioning agent 22 resulting in its adhesive properties, and the viscosity of the positioning agent 22, for example. In accordance with one example embodiment, the positioning agent 22 is applied to the surface of the mesh prosthesis with a loading dose of about 0.45 ml/in$^2$.

In accordance with one example embodiment, the step of applying the positioning agent 22 to a first side 24 of the surgical mesh prosthesis 20 (step 104a) is performed in the absence of drying the positioning agent 22 so the positioning agent 22 forms a non-dried coating on the surgical mesh prosthesis 20 that permits the surgical mesh prosthesis 20 to removably adhere to tissue 28 within the patient.

The step of positioning the surgical mesh 20 (step 106) can be performed in a variety of ways, as will be appreciated by the skilled artisan. For example, the step of positioning can include placing the first side 24 of the surgical mesh prosthesis 20, which is coated with positioning agent 22, in contact with the tissue 28 to cause the surgical mesh prosthesis 20 to removably and atraumatically adhere to the tissue 28. This step can be performed, for example, by using laparoscopic graspers to remove the mesh prosthesis 20 from the viscera atraumatically without damaging the bowel or omentum and placing the surgical mesh prosthesis 20 into contact with the tissue 28. In another example, the step of positioning the surgical mesh prosthesis 20 (step 106) can include positioning the surgical mesh prosthesis 20 by sliding the surgical mesh prosthesis 20 along the tissue 28 (e.g., at targeted tissue location 30) to a desired position without traumatizing the tissue 28.

It should be appreciated that although the surgical mesh prosthesis 20 can easily be slid and positioned upon application of external force due to the positioning agent 22, the surgical mesh prosthesis 20 otherwise remains in place once positioned due to the adhesion strength of the positioning agent 22. Thus, the positioning agent 22 provides the requisite adhesion force to maintain the surgical mesh prosthesis 20 in a stationary position at the targeted tissue location 30 without moving, against the forces of gravity, but the adhesion force provided by the positioning agent 22 is not so strong that the surgical mesh prosthesis 20 cannot be pulled off and removed without causing significant trauma to the tissue 28. In addition, or alternatively, the positioning agent 22 possesses the requisite dynamic viscosity to enable a user to apply an external force to the surgical mesh prosthesis 20 to reposition the surgical mesh 20 by sliding it due to the lubricity of the positioning agent 22; however, the dynamic viscosity of the positioning agent 22 is not so low as to allow the surgical mesh prosthesis 20 to slide out of position when there are no external forces applied (excluding gravity) and also not so high as to cause trauma to the tissue 28 when the surgical mesh prosthesis 20 is slid during forced repositioning. Thus, the positioning agent 22 is able to maintain the surgical mesh prosthesis 20 in place at the targeted tissue location against the force of gravity while allowing the surgical mesh prosthesis 20 to slide along the surface of the tissue 28 atraumatically when an additional external force is applied by the surgeon, for example.

As noted above, if desirable, the method of implanting the surgical mesh prosthesis 20 can include the step of repositioning the surgical mesh prosthesis 20 (step 108) against the targeted tissue location 30 without traumatizing the tissue 28. In one example embodiment, the repositioning step (step 108) can further include sliding the surgical mesh prosthesis 20 from a first location on the tissue 28 to reposition the surgical mesh prosthesis 20 to a second location on the tissue 28. In another example embodiment, the repositioning step 108 can further include peeling the surgical mesh prosthesis 20 away from a first location on the tissue 28 and placing the surgical mesh prosthesis 20 on a second location on the tissue 28. In accordance with one example embodiment, the positioning agent 22 enables the surgical mesh prosthesis 20 to be peeled away from the first location on the tissue 28 (e.g., a targeted tissue location 30) without substantially removing the mesothelium layer from the targeted tissue location 30. By the phrase "without substantially removing the mesothelium layer," what is meant is that the positioning agent 22 is made so that peeling away the surgical mesh prosthesis 20 may remove some negligible quantity of mesothelium cells; however, the mesothelium layer generally remains intact (and thus is not substantially removed) to a degree necessary to still function as an intact mesothelial layer.

In other words, the mesothelium produces a lubricating fluid that is released between adjacent layers, and provides a generally slippery, non-adhesive, and protective surface for the internal abdominal wall and the abdominal viscera so as to facilitate intracoelomic movement, as would be understood by those of skill in the art. The ability of the mesothelial layer, over which the positioning agent 22 permits the surgical mesh prosthesis 20 to adhere and slide, is not substantially compromised by the temporary adherence and/or sliding of the surgical mesh prosthesis 20. Those skilled in the art will further appreciate that in addition to positioning the surgical mesh prosthesis 20 at an optimal location over a hernia or other tissue defect, the positioning agent 22 facilitates sliding and repositioning to help the surgical mesh prosthesis 20 conform to the contour of the targeted tissue location 30 (e.g., by smoothing out any wrinkles in the surgical mesh prosthesis 20 resulting from rolling or sliding the surgical mesh prosthesis 20, which improves tissue contact of the surgical mesh prosthesis 20).

The positioning agents 22 of the present disclosure can be used in any surgical hernia repair in which it is desirable to position an implantable device (such as the surgical mesh prosthesis 20) against a targeted tissue location 30, including for example, surgical repair of inguinal or ventral hernias. The positioning agents 22 of the present disclosure can significantly reduce patient time in the operating room by minimizing, or eliminating, the requirement for a surgeon to measure and mark the patient and the implantable device, namely, the, surgical mesh 20 prosthesis, to ensure that the implanted device is centered correctly over a hernia or other tissue defect. In particular, the positioning agents 22 of the present disclosure enable a positioning agent-coated implantable prosthesis 20, 22 to be positioned at an optimal location against the hernia or other tissue defect, for example, by sliding the prosthesis 22 against the tissue 28 without traumatizing the tissue 28. In this way, the prosthesis 22 can easily be repositioned at an optimal location over the hernia or other tissue defect by sliding the prosthesis along the hernia or tissue defect without requiring lengthy measuring and marking, as is conventionally required to ensure that the prosthesis is properly aligned over the hernia or other tissue defect.

The adhesive strength of the positioning agents 22 enable an implantable prosthesis to be maintained in place against a targeted tissue location 30, and enable the implantable prosthesis to be removed and repositioned over a defect multiple times. Moreover, the viscosity of the positioning agents 22 enable an implantable prosthesis to be maintained in place against a targeted tissue location despite gravity, or slid into different positions, without the positioning agent 22 losing its ability to adhere the implantable prosthesis to the targeted tissue location 30. Though the viscosity of the positioning agents 22 permit the implantable prosthesis to be easily slid and repositioned against a targeted tissue location 30, the adhesive strength of the positioning agent 22 is maintained long enough so that the implantable prosthesis remains in place over the hernia or other tissue defect against the targeted tissue location 30, for example, until a tacker dispensing surgical tacks, or a stapler dispensing surgical staples, or surgical sutures, can be used to permanently fixate the prosthesis in place at the targeted tissue location 30. In this context, a permanent fixation is one that provides sufficient fixation for a sufficiently long period of time for the patient's body to permanently fix the surgical mesh prosthesis in place regardless of whether the surgical mesh prosthesis remains fixed in place for the natural life of the patient, or degrades and is eventually bio-absorbed by the patient's body. The ability of a positioning agent-coated prosthesis to be easily slid and repositioned, without having to remove and replace the prosthesis from the tissue surface, minimizes the risk of long term tissue adhesions due to inadvertent contact with the viscera that is likely to result when a prosthesis is removed away from the tissue at the site of the hernia or defect and replaced into a different position.

The following illustrative, non-limiting embodiments of a method of implanting a surgical mesh are provided, wherein the method includes positioning a surgical mesh prosthesis against a surface of a target tissue with a positioning agent disposed between the surgical mesh prosthesis and the surface of the target tissue, wherein the positioning agent has an adhesion strength adequate to maintain the surgical mesh prosthesis temporarily in place, otherwise unsupported, against the surface of the target tissue in the absence of setting or curing of the positioning agent. This embodiment may be modified so that the positioning agent is applied to the tissue of the targeted tissue location before positioning the surgical mesh prosthesis against the tissue, and/or the embodiment may be modified so that the positioning agent is applied to a first side of the surgical mesh prosthesis before positioning the surgical mesh against the tissue.

In accordance with this disclosure, the step of applying the positioning agent to the first side of the surgical mesh may be performed before the surgical mesh prosthesis is introduced into the patient (i.e., external application), or the step of applying the positioning agent to the first side of the surgical mesh prosthesis is performed using an applicator after the surgical mesh prosthesis is inserted into the patient (i.e., internal application). In accordance with this disclosure, the above method embodiments may be further modified so that the method of implanting a surgical mesh includes sliding the surgical mesh from a first location on the tissue to reposition the surgical mesh in a second location on the tissue, and/or it may further include sliding the surgical mesh prosthetic to remove the wrinkles and improve tissue contact of the mesh. Moreover, the methods of implanting a surgical mesh disclosed above may each further include peeling the surgical mesh prosthetic away from a first location on the tissue and placing the surgical mesh prosthesis in a second location on the tissue.

In accordance with this disclosure, the step of positioning further includes sliding the surgical mesh prosthesis along the tissue to the desired position without traumatizing the tissue, and/or it further includes peeling the surgical mesh prosthesis away from a first location on the tissue without traumatizing the tissue and placing the surgical mesh in a second location on the tissue. Also in accordance with this disclosure, the positioning agent temporarily maintains the mesh prosthesis in place, otherwise unsupported, against tissue until the mesh prosthesis is secured in place against the tissue during a subsequent fixation step. Thus, in accordance with this disclosure, all of the above method embodiments may further include the step of fixating (permanently) the mesh prosthesis in place against the tissue. In accordance with aspects of this disclosure, the surgical mesh prosthesis may be previously sterilized prior to the step of positioning the surgical mesh prosthesis.

In accordance with this disclosure, the method embodiments employ a positioning agent that has a viscosity adequate to enable slidable movement of the surgical mesh prosthesis along the tissue upon receipt of an external force (i.e., a non-gravitational external force) applied to the surgical mesh prosthesis in such a way that the sliding movement of the surgical mesh prosthesis is atraumatic to the tissue. Furthermore, the positioning agent has a viscosity under shear that is sufficient to allow for the mesh prosthesis to slide for repositioning, and the viscosity does not irreversibly change, absent an external application of force, temperature differences or moisture absorption, by more than 500% over a duration of between 1 minutes and 30 minutes. In accordance with method embodiments of this disclosure, the positioning agent may have a viscosity of greater than 150 Cps and/or less than 26,000,000 Cps when tested at 0.1 $S^{-1}$ and 23° C. In accordance with other method embodiments of this disclosure, the positioning agent has a viscosity of greater than 50 Cps and/or less than 2,530,000 Cps when tested at 9.77 $S^{-1}$ and 23° C.

In accordance with this disclosure, a method of positioning a surgical mesh—prosthesis against a targeted tissue location is provided. This method includes providing a surgical mesh prosthesis; applying a positioning agent to a first side of the surgical mesh prosthesis in the absence of drying the positioning agent to form a non-dried coating that permits the surgical mesh prosthesis to removably adhere to a tissue within the patient; and placing the first side of the surgical mesh prosthesis in contact with the tissue to cause the surgical mesh prosthesis to removably adhere to the tissue.

In accordance with this disclosure, such a method of positioning a surgical mesh prosthesis against a targeted tissue location may further include positioning the surgical mesh prosthesis by sliding the surgical mesh prosthesis along the targeted tissue location to a desired position without traumatizing the tissue, and/or positioning the surgical mesh prosthesis by peeling the surgical mesh prosthesis away from the targeted tissue location without traumatizing the tissue and placing it against the targeted tissue location in a desired position.

In accordance with this disclosure, the following method embodiments are described with their modifications. Thus, in accordance with a first non-limiting method embodiment, a method of implanting a surgical mesh prosthesis comprises the steps of: (a) positioning a surgical mesh prosthesis against a surface of a target tissue with a positioning agent disposed between the surgical mesh prosthesis and the surface of the target tissue, wherein the positioning agent has an adhesion strength adequate to maintain the surgical mesh prosthesis temporarily in place, otherwise unsupported, against the target tissue in the absence of setting or curing of the positioning agent. In accordance with a second non-limiting method embodiment, the first non-limiting method embodiment is modified so that the positioning agent is applied to the surface of the target tissue before positioning the surgical mesh prosthesis against the tissue. In accordance with a third non-limiting method embodiment, the first and second method embodiments are further modified so that the positioning agent is applied to a first side of the surgical mesh prosthesis before positioning the surgical mesh prosthesis against the surface of the tissue.

In accordance with a fourth non-limiting embodiment of the method, the third non-limiting embodiment is further modified so that the step of applying the positioning agent to the first side of the surgical mesh prosthesis is performed before the surgical mesh is introduced into the patient. In accordance with a fifth non-limiting method embodiment, the third non-limiting method embodiment is further modified so that the step of applying the positioning agent to the first side of the surgical mesh is performed using an applicator after the surgical mesh prosthesis is inserted into the patient. In accordance with a sixth non-limiting embodiment of the method, the first, second, third and fourth non-limiting embodiments are modified to further include sliding the surgical mesh prosthesis from a first location on the tissue to reposition the surgical mesh prosthesis in a second location on the tissue.

In accordance with a seventh non-limiting embodiment, the first, second, third, fourth, fifth and sixth embodiments may be modified to further include sliding the surgical mesh prosthesis to remove the wrinkles and improve tissue contact of the mesh prosthesis. In accordance with an eighth non-limiting embodiment, the first, second, third, fourth, fifth, sixth and seventh embodiments may be further modified to further include peeling the surgical mesh prosthesis away from a first location on the tissue and placing the surgical mesh prosthesis in a second location on the tissue. In accordance with a ninth non-limiting embodiment, the first, second, third, fourth, fifth, sixth, seventh, and eighth non-limiting embodiments are further modified so that the step of positioning further includes sliding the surgical mesh prosthesis along the tissue to the desired position without traumatizing the tissue. In accordance with a tenth non-limiting embodiment of the method, the first, second, third, fourth, fifth, sixth, seventh, eighth and ninth non-limiting embodiments are further modified so that the step of positioning further comprises peeling the surgical mesh prosthesis away from a first location on the tissue without traumatizing the tissue and placing the surgical mesh prosthesis in a second location on the tissue.

In accordance with an eleventh non-limiting embodiment of the method, the first, second, third, fourth, fifth, sixth, seventh, eighth, ninth and tenth non-limiting embodiments are further modified so that the positioning agent is non-setting. In accordance with a twelfth non-limiting embodiment of the method, the first, second, third, fourth, fifth, sixth, seventh, eighth, ninth, tenth and eleventh non-limiting embodiments are modified so that the positioning agent temporarily maintains the mesh prosthesis in place, otherwise unsupported, against tissue until the mesh prosthesis is secured in place against the tissue during a subsequent fixation step. In accordance with a thirteenth non-limiting embodiment of the method, the first, second, third, fourth, fifth, sixth, seventh, eighth, ninth, tenth, eleventh and twelfth non-limiting embodiments are further modified to further include fixating the mesh prosthesis in place against the tissue.

In accordance with a fourteenth non-limiting embodiment of the method, the first, second, third, fourth, fifth, sixth, seventh, eighth, ninth, tenth, eleventh, twelfth and thirteenth non-limiting embodiments are further modified so that the positioning agent has a viscosity adequate to enable slidable movement of the surgical mesh prosthesis along the tissue upon receipt of external force (i.e., a non-gravitational external force) applied to the surgical mesh prosthesis and so that the sliding movement of the surgical mesh prosthesis is atraumatic to the tissue. In accordance with a fifteenth non-limiting embodiment of the method, the first, second, third, fourth, fifth, sixth, seventh, eighth, ninth, tenth, eleventh, twelfth, thirteenth and fourteenth non-limiting embodiments are further modified so that the positioning agent has a viscosity under shear that is sufficient to allow for the mesh prosthesis to slide for repositioning. In accordance with a sixteenth non-limiting embodiment of the method, the first, second, third, fourth, fifth, sixth, seventh, eighth, ninth, tenth, eleventh, twelfth, thirteenth, fourteenth and fifteenth non-limiting embodiments are further modified so that the positioning agent has a viscosity that does not irreversibly change, absent an external application of force, temperature differences or moisture absorption, by more than 500% over a duration of between 1 minutes and 30 minutes.

In accordance with a seventeenth non-limiting embodiment of the method, the first, second, third, fourth, fifth, sixth, seventh, eighth, ninth, tenth, eleventh, twelfth, thirteenth, fourteenth, fifteenth and sixteenth non-limiting embodiments are further modified so that the positioning agent has a dynamic viscosity of greater than 150 Cps when tested at $0.1 \text{ S}^{-1}$ and $23°$ C. In accordance with an eighteenth non-limiting embodiment of the method, the first, second, third, fourth, fifth, sixth, seventh, eighth, ninth, tenth, eleventh, twelfth, thirteenth, fourteenth, fifteenth, sixteenth and seventeenth non-limiting embodiments are further modified so that the positioning agent has a dynamic viscosity less than 26,000,000 Cps when tested at $0.1 \text{ S}^{-1}$ and $23°$ C. In accordance with a nineteenth non-limiting embodiment of the method, the first, second, third, fourth, fifth, sixth, seventh, eighth, ninth, tenth, eleventh, twelfth, thirteenth, fourteenth, fifteenth, sixteenth, seventeenth, and eighteenth non-limiting embodiments are further modified so that the positioning agent has a dynamic viscosity of greater than 50 Cps when tested at $9.77 \text{ S}^{-1}$ and $23°$ C. In accordance with a twentieth non-limiting embodiment of the method, the first, second, third, fourth, fifth, sixth, seventh, eighth, ninth, tenth, eleventh, twelfth, thirteenth, fourteenth, fifteenth, sixteenth, seventeenth, eighteenth and nineteenth non-limiting embodiments are further modified so that the positioning agent has a dynamic viscosity of less than 2,530,000 Cps when tested at $9.77 \text{ S}^{-1}$ and $23°$ C. Furthermore, in accordance with a twenty-first non-limiting embodiment of the method, the first, second, third, fourth, fifth, sixth, seventh, eighth, ninth, tenth, eleventh, twelfth, thirteenth, fourteenth, fifteenth, sixteenth, seventeenth, eighteenth, nineteenth and twentieth non-limiting embodiments are further modified so that the surgical mesh prosthesis is previously sterilized prior to the step of positioning the surgical mesh prosthesis.

In accordance with a twenty-second non-limiting method embodiment of this disclosure, a method of positioning a surgical mesh prosthesis against a targeted tissue location is provided, wherein the method includes the steps of: (a) providing a surgical mesh prosthesis; (b) applying a positioning agent to a first side of the surgical mesh prosthesis in the absence of drying the positioning agent to form a non-dried coating that permits the surgical mesh prosthesis to removably adhere to a tissue within the patient; and (c) placing the first side of the surgical mesh prosthesis in contact with the tissue to cause the surgical mesh prosthesis to removably adhere to the tissue. In accordance with a twenty-third non-limiting method embodiment, the twenty-second non-limiting method embodiment is modified so that it further includes positioning the surgical mesh prosthesis by sliding the surgical mesh prosthesis along the targeted tissue location to a desired position without traumatizing the tissue. In accordance with a twenty-fourth non-limiting method embodiment, the twenty-second and twenty-third non-limiting embodiments are further modified to further include positioning the surgical mesh prosthesis by peeling the surgical mesh prosthesis away from the targeted tissue location without traumatizing the tissue and placing it against the targeted tissue location in a desired position.

ILLUSTRATIVE NON-LIMITING EXAMPLES

Example 1

A laparoscopic surgery trainer (Lap Trainer) was lined with plastic and a section of porcine ribs was attached to the top of the sample chamber using zip ties. A 2"×0.5" defect was made in the center of the underside of the rib cage using a scalpel. Two ml of glycerin was deposited, as positioning agent, onto the rough surface of a 3"×3" piece of commercially available C-QUR® mesh (Atrium Medical Corporation, Hudson, N.H.). As will be appreciated by those skilled in the art, C-QUR® mesh is a polypropylene mesh provided with a coating derived from fish oil containing a mixture of triglycerides and omega 3 fatty acids. A gloved finger was then used to evenly spread the glycerin over the surface of the mesh prosthesis. The glycerin coated mesh prosthesis was then rolled up and inserted through a 10 mm trocar and into the chamber of the Lap Trainer. Laparoscopic graspers were used to unroll the mesh prosthesis, lift it up and place it over the defect in the porcine ribs with the rough side contacting the tissue. The glycerin worked very well to both assist in putting the mesh prosthesis through the trocar as well as temporarily adhering the mesh prosthesis to the underside of the porcine ribs and over the surgically created defect. The mesh prosthesis could be repositioned by sliding into another position or by peeling it down and placing it in a new position.

Comparative Example A

A 4"×4" piece of C-QUR® mesh was applied to a polytetrafluoroethylene (PTFE) release liner and corona treated (i.e., subjected to a surface treatment employing a visible electrical discharge that occurs when a high voltage, high frequency electrical potential is applied to a small diameter electrode in relatively close proximity to an electrical ground). The mesh prosthesis was then hand coated on the rough side with a positioning agent having a 2% CMC/1% Glycerol formulation (wherein CMC is an abbreviation for sodium carboxymethyl cellulose). The positioning agent coated C-QUR® mesh prosthesis was then applied to the back of a gloved hand (Nitrile). The hand was then inverted and the positioning agent coated C-QUR® mesh prosthesis demonstrated sufficient adhesion to remain attached to the surface of the glove against the force of gravity. The mesh prosthesis was then peeled off and there was noticeable resistance between the mesh prosthesis and the glove that was generated by the CMC formulation. The experiment was then repeated using a 4"×4" piece of C-QUR® mesh that was not corona treated, and similar results were observed. The similar results obtained in this experiment indicate that corona treatment of the mesh prosthesis will not be necessary for use of positioning agents comprising a 2% CMC/1% Glycerol formulation.

Comparative Example B

Four different variations of positioning agents were prepared and evaluated using a force of detachment test (FOD) with the commercially available C-QUR® omega-3 fatty acid (O3FA) coated mesh products (Atrium Medical Corporation, Hudson, N.H.). The positioning agents were prepared using 7HF CMC (0.7 D.S., Ashland Specialty Ingredients), 12M31P CMC (1.2 D.S., Ashland Specialty Ingredients), glycerin (Sigma Aldrich) and Sterile Water for Injection (Baxter), which is abbreviated "SWFI." The details of the formulations of these sample positioning agents can be found in Table 1.

TABLE 1

Exemplary Formulations

| Sample | 7HF CMC* | 12M31P CMC** | Glycerin | SWFI |
|---|---|---|---|---|
| 1 | 4% | — | 2% | 94% |
| 2 | — | 4% | 2% | 94% |
| 3 | — | 6% | 3% | 91% |
| 4 | — | — | 100% | — |

*7HF CMC is a grade of CMC formulation (viscosity 1500-3000 Cps at 25° C.).
**12M31P CMC is a grade of CMC formulation (viscosity 800-3100 Cps at 25° C.).

Squares measuring 1"×1" were cut out of the C-QUR® O3FA coated mesh. One subset of the samples was then placed on a PTFE release liner and corona treated. Each of the positioning agents were then applied to the rough side of both the corona treated and untreated 1"×1" sections of C-QUR® mesh at 200 mg/in$^2$ loadings. After each of the positioning agents were loaded onto the C-QUR® mesh samples they were attached to sections of prepared bovine intestine. The control groups in this experiment consisted of C-QUR® mesh as well as C-QUR® mesh that had previously been made with 7HF and 12M31P grades of CMC formulations and dried. After a standardized tissue contact time of 3 minutes, a Chatillon® gage was then used to pull the samples off of the tissue at a rate of 45 in/min with a lap shear configuration. The force of detachment data, which measures shear strength of the positioning agents, can be seen in FIG. 5.

From FIG. 5 it can be seen that all of the positioning agent samples are substantially equivalent to the control C-QUR® mesh in terms of force of detachment (i.e., shear strength). These values are all statistically lower than the pre-dried control samples that were made using the 7HF and 12M31P grades of CMC. This data demonstrates that positioning agents provide a temporary tissue attachment mechanism that will be able to freely slide on the tissue to aid in positioning and repositioning of the mesh. The pre-dried samples have a higher force of detachment, which may require them to be removed and replaced rather than permit sliding for repositioning. The work described herein demonstrates that the application of a positioning agent to C-QUR® mesh greatly increases its ability to adhere over a tissue defect while being slid into position when compared to conventional C-QUR® mesh.

Comparative Example C

Four different variations of positioning agents were prepared and evaluated using a general tissue adherence test with the commercially available C-QUR® O3FA coated mesh products (Atrium Medical Corporation, Hudson, N.H.). The positioning agents were prepared using 7HF CMC (0.7 D.S., Ashland Specialty Ingredients), 12M31P CMC (1.2 D.S., Ashland Specialty Ingredients), glycerin (Sigma Aldrich) and Sterile Water for Injection (SWFI) (Baxter). The details of the formulations of the sample positioning agents can be found in Table 1 above.

3.5"×3.5" C-QUR® Anatomical Plane of Dissection (APD) shaped controls, previously coated and dried self-adhering C-QUR® mesh (both 7HF and 12M31P CMC), and C-QUR® mesh with CMC-positioning agents were then evaluated by simulating laparoscopic placement of each sample over a defect in a sample of rib tissue. The APD shape is similar to a square except that it has rounded corners. A 4 cm circular defect was cut into the center of a 6"×7" (approximate) section of porcine ribs to simulate an over-sized abdominal wall defect for the size mesh being tested. The rib section was positioned on the top inner surface of the laparoscopic trainer (3-Dmed Large Body MITS TRLCD05) with the concave side of the ribcage facing down, exposing it to the cavity in the trainer. The rib section was secured to the trainer surface. The rib tissue was hydrated continuously throughout the experiment by applying 0.9% Saline solution to the surface between each sample.

To conduct this testing, the samples were prepared as described in Table 2. An appropriate amount of the positioning agent was deposited onto the mesh pieces and they were rolled tightly with the rough-side of the mesh facing inward. The mesh samples were then delivered through an 11 mm trocar to the interior of the laparoscopic trainer cavity. Once the samples were placed inside the lap trainer, the samples were unrolled and positioned over the 4 mm defect that had been created in the tissue. This was done with the rough-side of the mesh against the tissue using 5 mm laparoscopic graspers. The samples were assessed to determine if the placement mechanism was sufficient to support the weight of the mesh over the over-sized defect, and if the sample could be removed and replaced over the defect a second time, and if the sample could be slid into a different position if necessary.

TABLE 2

Sample groups for Laparoscopic Trainer Simulation Testing

| Sample | Coating Type | Coating Load | Notes |
|---|---|---|---|
| C-QUR ® mesh Control | No coating | N/A | Will not adhere to the non-horizontal rib tissue surface unaided. |
| Pre Dried C-QUR ® mesh (self-adhering mesh) | 7HF CMC | 16.6 mg/in$^2$ | Can be applied to non-horizontal rib tissue surface and left unsupported, can be removed and repositioned. Difficulty sliding. |
| Pre Dried C-QUR ® mesh (self-adhering mesh) | 12M31P CMC | 16.6 mg/in$^2$ | Can be applied to non-horizontal rib tissue surface and left unsupported, can be removed and repositioned. Difficulty sliding. |
| C-QUR ® mesh coated with 6% solids Gel of Sample 1 of Table 1 | 7HF CMC | 200 mg/in$^2$ | Can be applied to non-horizontal rib tissue surface and left unsupported, can be removed or slid and repositioned without difficulty. |
| C-QUR ® mesh coated with 6% solids Gel of Sample 2 of Table 1 | 12M31P CMC | 200 mg/in$^2$ | Can be applied to non-horizontal rib tissue surface and left unsupported, can be removed or slid and repositioned without difficulty. |
| C-QUR ® mesh coated with 9% solids Gel of Sample 3 of Table 1 | 12M31P CMC | 200 mg/in$^2$ | Can be applied to non-horizontal rib tissue surface and left unsupported, can be removed or slid and repositioned without difficulty. |
| C-QUR ® mesh coated with 100% solids (glycerin) of Sample 4 of Table 1 | Glycerin | 200 mg/in$^2$ | Can be applied to non-horizontal rib tissue surface and left unsupported, can be removed or slid and repositioned without difficulty. |
| C-QUR ® mesh wetted with 0.9% Saline | N/A | Submerged, no unit measured | Will not adhere to the non-horizontal rib tissue surface unaided. |

This experiment demonstrates that C-QUR® mesh coated with the positioning agent adheres effectively to the porcine rib tissue surface, by adhering to all areas surrounding the defect even with minimal overlap. Samples of C-QUR® mesh with CMC positioning agent could be placed over the defect, removed and replaced a second time without a noted loss in tissue adherence. Due to the gel-like properties (i.e., lubricity and adherence) of the positioning agent, these samples could also be repositioned by sliding them into a different or more optimal location without removing them. The positioning agents appear to be as effective in terms of adequate adherence strength as previously coated and dried Self-Adhering C-QUR® mesh (a polypropylene mesh provided with a coating derived from fish oil containing a mixture of triglycerides and omega 3 fatty acids, and further provided with a pre-dried CMC based material to give it self-adhering properties) samples with coating loadings of approximately 16.6 mg/in$^2$. Both the Self-Adhering C-QUR® samples and C-QUR® samples coated with positioning agents were effective enough to maintain the position of the mesh prosthesis, thus serving the purpose of aiding in mesh prosthesis placement during a laparoscopic procedure. With the extreme size defect tested, conventional C-QUR® or C-QUR® mesh that had been hydrated in saline were unable to support the weight of the mesh unaided.

Comparative Example D

An experiment was conducted to determine if positioning agents would work successfully at a temperature of 37° C. and 100% RH. To conduct this experiment, a laparoscopic trainer (3-Dmed Large Body MITS TRLCD05) was set up so that temperature and humidity could be controlled and monitored. The interior of the laparoscopic trainer was first covered using plastic tank lining material to protect the interior from contact with tissue, fluids, and other wet materials. A hot plate was then placed inside the chamber and set to 100° C. A glass petri dish was then filled with water and placed on the hot plate to provide humidity to the chamber. A 4 cm circular defect was cut into the center of a 6"×7" (approximate) section of porcine ribs to simulate an over-sized abdominal wall defect for the size mesh being tested (3.5"×3.5"). The rib section was positioned on the top inner surface of the laparoscopic trainer with the concave side of the ribcage facing down, exposing it to the cavity in the trainer. The rib section was secured to the trainer surface using zip-ties that were threaded through the tissue and open ports on the top and sides. The entire laparoscopic surgery trainer was then wrapped in plastic to prevent loss of heat and humidity. The chamber and the tissue were then equilibrated for a period of 3 hours to attain a temperature of 37° C. and relative humidity (RH) of 100%.

Four different variations of positioning agents were prepared and evaluated using this body temperature tissue adherence test in combination with Atrium's C-QUR® O3FA coated mesh products. The positioning agents were prepared using various ratios of 7HF CMC (0.7 D.S., Ashland Specialty Ingredients), 12M31P CMC (1.2 D.S., Ashland Specialty Ingredients), glycerin (Sigma Aldrich) and Sterile Water for Injection (SWFI) (Baxter). The details of the formulations of the sample positioning agents can be found in Table 1 above.

3.5"×3.5" C-QUR® Anatomical Plane of Dissection (APD) shaped controls, previously coated and dried self-adhering C-QUR® mesh (both 7HF and 12M31P CMC), and C-QUR® mesh with CMC-positioning agents were then evaluated by simulating laparoscopic placement of each sample over a defect in a sample of rib tissue while being maintained at 37° C.

To conduct this testing, the samples were prepared as described in Table 2 above. Two ml of the room temperature positioning agents were dispensed onto the surface of the 3.5"×3.5" APD shaped mesh samples leading to a positioning agent coating density of 200 mg/in$^2$. The samples were then rolled tightly with the rough-side of the mesh facing inward, and delivered through a 12 mm trocar to the interior of the laparoscopic trainer cavity. Once the samples were placed inside the lap trainer, the samples were unrolled and positioned over the 4 mm defect that had been created in the tissue. This was done with the rough-side of the mesh against the tissue using 5 mm laparoscopic graspers. The samples were assessed to determine if the placement mechanism was sufficient to support the weight of the mesh over the over-sized defect, and to determine if the sample could be removed and replaced over the defect a second time, and to determine if the sample could be slid into a different position if necessary. The rib tissue was hydrated continuously throughout the experiment by applying 0.9% Saline solution to the surface between each sample.

This experiment demonstrates that C-QUR® mesh coated with the positioning agent adheres effectively to the 37° C. tissue surface. When an extreme case was presented by covering a 4 cm circular defect (1.57 inch) with a 3.5"×3.5" APD shaped mesh sample, the positioning agent-coated prosthetic device adhered to all areas surrounding the defect even with minimal overlap. Samples of C-QUR® mesh with CMC positioning agents could be placed over the defect removed and replaced a second time without a noted loss in tissue adherence. Due to the gel-like properties (i.e., lubricity and adherence) of the positioning agent, these samples could also be repositioned by sliding them into a different or more optimal location without removing them. The positioning agents appear to be as effective, in terms of adherence to tissue surfaces, as previously coated and dried Self-Adhering C-QUR® mesh samples (i.e., C-QUR® mesh provided with a pre-dried CMC based material that gives the mesh self-adhering properties, but which does not give the mesh lubricity properties) with coating loadings of approximately 16.6 mg/in$^2$. Both the Self-Adhering C-QUR® mesh samples and C-QUR® mesh samples coated with positioning agents were effective enough to maintain the position of the mesh prosthesis over a 4 mm defect, thus serving the purpose of aiding in mesh placement during a laparoscopic procedure. When the extreme size defect is tested, conventional C-QUR®, or self adhering C-QUR® that had been hydrated in saline, were unable to support the weight of the mesh unaided due to inadequate adherence properties, while the positioning agent-coated C-QUR® mesh exhibited satisfactory adherence to surrounding tissues to maintain its position over the defect.

Comparative Example E

Positioning agents were evaluated with various commercially available meshes. A section of porcine abdominal wall was inverted and attached to a flat supporting structure. Excess fat and loose tissue was removed from the abdominal wall. 0.9% saline solution was used to clean and moisten the tissue. Commercially available hernia meshes were then applied to the tissue to determine if they had enough adhesive strength to support their own weight without the use of a positioning agent. Samples that were 4"×6" or smaller were used as is, and samples that were larger were cut to match the 4"×6" Anatomical Plane of Dissection (APD) size and shape of the Atrium samples. When applied to the tissue without the use of a positioning agent, the only mesh samples tested that had enough adhesive strength to support their weight were the PROCEED® mesh (an oxidized regenerated cellulose fabric laminated on a nonabsorbable polypropylene mesh, which is encapsulated by a polydioxanone polymer) from Ethicon and the Parietex PROGRIP® mesh (a monofilament polyester mesh with resorbable polylactic acid gripping system) from Covidien. Although both of these materials adhered on their own, neither of them was able to slide for repositioning. A listing of the meshes tested without the positioning agent can be seen in Table 3.

TABLE 3

Testing of commercial hernia meshes without the use of positioning agents

| Mesh Manufacturer | Product | Mesh Sample Size | Does bare Mesh adhere? | Does Bare Mesh slide? |
| --- | --- | --- | --- | --- |
| Tyco/Covidien | Parietex Composite | 4" × 6" APD | N | N/A |
| Davol | SEPRAMESH ® | 4" × 6" APD | N | N/A |
| Ethicon | PROCEED ® | 3" × 6" | Y | N |
| Aspide Medical | SURGIMESH ® | 10 cm round | N | N/A |
| Atrium | C-QUR ® | 4" × 6" APD | N | N/A |
| Bard (Davol) | COMPOSIX ® L/P | 4.5 in round | N | N/A |
| Ethicon | PHYSIOMESH ® | 4" × 6" ellipse | N | N/A |
| Atrium | PROLITE ® | 4" × 6" APD | N | N/A |
| Atrium | C-QUR ® FX | 4" × 6" APD | N | N/A |
| Atrium | C-QUR ® MOSAIC ™ | 4" × 6" APD | N | N/A |
| Tyco/Covidien | Parietex PROGRIP ® | 4" × 6" | Y | N |

Parietex Composite mesh is a monofilament polyester mesh with resorbable polylactic acid gripping system.
SEPRAMESH ® mesh is a polypropylene mesh with a hydrogel safety coating.
PROCEED ® mesh is an oxidized regenerated cellulose fabric laminated on a nonabsorbable polypropylene mesh, which is encapsulated by a polydioxanone polymer.
SURGIMESH ® is a non-woven polypropylene mesh.

TABLE 3-continued

Testing of commercial hernia meshes without the use of positioning agents

| Mesh Manufacturer | Product | Mesh Sample Size | Does bare Mesh adhere? | Does Bare Mesh slide? |
|---|---|---|---|---|

C-QUR ® mesh is a polypropylene mesh provided with a coating derived from fish oil containing a mixture of triglycerides and omega 3 fatty acids.
COMPOSIX ® L/P mesh has a large pore polypropylene matrix on one side and a sub-micronic expanded polytetrafluoroethylene (ePTFE) layer on the other side.
PHYSIOMESH ® is a composite mesh provided with MONOCRYL ® (poliglecaprone 25) suture polymer on both sides.
PROLITE ® mesh is a knitted polypropylene monofilament mesh material.
C-QUR ® FX mesh is an Omega-3 coated filament polypropylene mesh.
C-QUR ® MOSAIC ™ is an Omega-3 fatty acid coated polypropylene mesh.
Parietex PROGRIP ® mesh is a monofilament polyester mesh with resorbable polylactic acid gripping system.

A positioning agent was then made formulated with 6% Carboxymethyl Cellulose, 3% Glycerin and 91% water. The positioning agent was dispensed on the commercially available meshes at a loading of 0.45 ml/in². The coated mesh samples were tightly rolled with the positioning agent coated side facing in to simulate insertion through a trocar or incision site. The coated mesh was unrolled and adhered to the inverted porcine abdominal wall. After the coated mesh was adhered to the abdominal wall, an attempt was made to reposition it by sliding. Finally, the coated mesh was then left unsupported for 30 minutes to determine if the positioning agent could support the weight of the mesh for an extended period of time. A listing of the commercial meshes tested with the positioning agents can be found in Table 4.

TABLE 4

In-Vitro Testing of commercial hernia meshes with the use of a positioning agent

| Mesh Manufacturer | Product | Positioning Agent Applied to Mesh (mL) | Mesh Sample Size | Does initial placement adhere? (y/n) | Does sample slide easily? (Y/N) | 30 min (pass/fail) |
|---|---|---|---|---|---|---|
| Tyco/Covidien | Parietex Composite | 10 | 4" × 6" APD | Y | Y | pass |
| Davol | SEPRAMESH ® | 10 | 4" × 6" APD | Y | Y | pass |
| Ethicon | PROCEED ® | 8 | 3" × 6" | Y | Y | pass |
| Aspide Medical | SURGIMESH ® | 5.5 | 10 cm round | Y | Y | pass |
| Atrium | C-QUR ® | 10 | 4" × 6" APD | Y | Y | pass |
| Bard (Davol) | COMPOSIX ® L/P | 7 | 4.5 in round | Y | Y | pass |
| Ethicon | PHYSIOMESH ® | 8.5 | 4" × 6" ellipse | Y | Y | pass |
| Atrium | PROLITE ® | 10 | 4" × 6" APD | Y | Y | pass |
| Atrium | C-QUR ® FX | 10 | 4" × 6" APD | Y | Y | pass |
| Atrium | C-QUR ® MOSAIC ™ | 10 | 4" × 6" APD | Y | Y | pass |
| Tyco/Covidien | Parietex PROGRIP ® | 11 | 4" × 6" | Y | N | pass |

When the positioning agent 22 was applied to various commercially available hernia meshes that would not adhere on their own, all of the positioning agent-coated meshes were able to adhere unsupported to porcine abdominal wall as evident from Tables 3 and 4. Samples could be removed and replaced or slid for repositioning, and all samples remained unsupported for an extended period of time (i.e., 30 min). When the positioning agent 22 was applied to the PROCEED® mesh, which was previously able to remain unsupported on its own, the positioning agent-coated PROCEED® mesh was then able to slide for repositioning. When the positioning agent 22 was applied to the Parietex PROGRIP® mesh, the positioning agent-coated Parietex PROGRIP® mesh behaved similar to how it behaved without the positioning agent, which is that it would not slide. Due to the mechanical interlock mechanism that Parietex PROGRIP® uses for tissue attachment, the Parietex PROGRIP® mesh was unable to slide for repositioning even when coated with positioning agent. Positioning agents have been shown, as evident from the tests reported herein, to be useful with various sizes, shapes, densities and configurations of commercially available hernia meshes.

Comparative Example F

Various commercially available medical lubricants, creams, gels and pastes were evaluated as positioning agents in comparison to 6% and 9% solids CMC/glycerin in aqueous solvent (water) as positioning agents. The various samples were evaluated by dispensing 5 ml of the sample on a 3.5"×3.5" APD shaped piece of Atrium MOSAIC™ mesh. Those skilled in the art will appreciate that the MOSAIC™ mesh is an omega 3 fatty acid coated propylene mesh for use in open and laparoscopic hernia repair that has a lighter coating compared to C-QUR® mesh. The coated MOSAIC™ mesh was then rolled, with the coated side facing in to simulate insertion through a trocar or incision site. The coated MOSAIC™ mesh was then unrolled and placed onto a section of porcine abdominal wall that had been inverted and attached to a flat supporting structure. Excess fat and loose tissue had been removed from the abdominal wall and 0.9% saline solution was used to clean and moisten the tissue. The ability of the sample loaded mesh to support its own weight, to slide for repositioning and to adhere for an extended period of time was evaluated. The rheology of the samples was then tested by running a shear rate sweep from 0.1-3000 $S^{-1}$ at 23° C. using an Anton Paar MCR 301 rheometer. The viscosity readings at 0.1 $S^{-1}$ and 9.77 S$^{-1}$ were recorded for each of the individual samples. The data can be found in Table 5.

dural variations were evaluated to determine the optimum product configurations for the positioning agents.

TABLE 5

Commercially available medical gels

| Gel Manufacturer | Product | Does initial placement adhere? (y/n) | Does sample slide easily? (Y/N) | 15 min (pass/fail) | Viscosity CPS 0.1 1/s | Viscosity CPS 9.77 1/s |
|---|---|---|---|---|---|---|
| N/A | Bare Mesh Control | N | N/A | N/A | N/A | N/A |
| Atrium | 6% CMC Formulation | Y | Y | pass | 4,420 | 3,100 |
| MPM Medical | Regenecare | Y | Y | pass | 25,800 | 8,680 |
| DeRoyal | Multidex Gel | Y | Y | pass | 50,000 | 49,200 |
| Paddock Labs | Glutose15 | Y | Y | pass | 87,000 | 10,700 |
| Savage Labs | Surgilube | Y | Y | pass | 96,600 | 17,700 |
| Atrium | 9% CMC Formulation | Y | Y | pass | 115,000 | 29,800 |
| McKesson | Lubricating Jelly | Y | Y | pass | 245,000 | 16,300 |
| Medline | Carrasyn | Y | Y | pass | 357,000 | 8,020 |
| Invacare | Lubricating Jelly | Y | Y | pass | 375,000 | 8,760 |
| Molnlycke health care | Normlgel | Y | Y | pass | 504,000 | 12,100 |
| ConvaTec | SAF-Gel | Y | Y | pass | 571,000 | 15,600 |
| ConvaTec | DuoDERM (gel) | Y | Y | pass | 587,000 | 38,500 |
| Hollister Woundcare | Restore | Y | Y | pass | 591,000 | 17,200 |
| Molnlycke health care | Hypergel | Y | Y | pass | 723,000 | 15,400 |
| Gentell | Gentell Hydrogel | Y | Y | pass | 737,000 | 13,800 |
| Smith&Nephew | Solosite | Y | Y | pass | 827,000 | 50,200 |
| SteadMed | Elta SilverGel | Y | Y | pass | 960,000 | 20,400 |
| Coloplast | Woun'Dres | Y | Y | pass | 1,280,000 | 33,700 |
| ConvaTec | DuoDERM (paste) | Y | N | pass | 3,560,000 | 143,000 |

Regenecare ® is a procollagen/lidocaine hydrogel that also contains aloe vera and benzehonium chloride, carbomer, glycerin, iodopropynyl butylcarbamate, sodium hyaluronate, and triethanolamine.
Multidex ® Gel contains maltodextrin and 1% ascorbic acid.
Glutose 15 is a gel containing water, 40% dextrose (d-glucose), glycerin, a flavoring agent and preservatives.
Surgilube is a gel containing hypromellose, propylene glycol and water.
McKesson lubricating jelly contains carbopol resin and sodium hydroxide.
Carrasyn ® hydrogel contains acemannan as well as aloe vera, carbomer, citric acid, edetate disodium, imidurea, L-glumatic acid, methylparaben, panthenol, polyvinylpyrrolidone, potassium sorbate, water, sodium benzoate, sodium chloride, sodium metabisulfite and trolamine.
Invacare lubricating jelly is a water soluble lubricant.
Normlgel ® contains sodium chloride, water and xantham gum.
SAF-gel contains water, propylene glycol, carbomer 940, triethanolamine, boric acid, sodium/calcium alginate, potassium sorbate, DMDM hydantoin and sodium carboxymethylcellulose.
DuoDerm ® gel contains pectin and sodium carboxymethylcellulose, which are hydrocolloids, in a clear, viscous vehicle.
Restore hydrogel contains water, glycerin, sodium polyacrylate, propylene glycol, hyaluronic acid, sodium metabisulfite, methylparaben, and propylparaben.
Hypergel ® contains 20% sodium chloride, water and xanthan gum.
Gentell ® hydrogel contains water, aloe vera extract, sorbitol, carbomer, triethanolamine, propylene glycol, imidazolidinyl urea, methylparaben and allantoin.
Solosite ® gel is a hydrogel that contains water, glycerol, an absorbent polymer, allantoin, and an antiseptic preservative.
Elta ® SilverGel is a silver antimicrobial hydrogel containing water and a proprietary formulation.
Woun'Dres ® collagen hydrogel contains water, collagen, panthenol, allantoin, tetrasodium EDTA, carbomer, citric acid, triethanolamine, methylparaben, imidazolidinyl urea, propylparaben.
DuoDerm ® paste is a hydrocolloid paste that includes gelatin, pectin, mineral oil, polyethylene, and carboxymethylcellulose.

Medical lubricants, creams, gels and pastes that ranged in viscosity from 4,420 Cps to 3,560,000 Cps at 0.1 S$^{-1}$ at 23° C. provided sufficient adhesion to the tissue to allow the weight of the coated mesh to be supported by the coating for an extended period of time (15 minutes). All of the samples tested could be either removed and replaced or slid over the tissue easily for repositioning except for the DUODERM® paste. The DUODERM® paste material had a viscosity of 3,560,000 CPS at 0.1 and 23° C. and could be removed and replaced but would not slide easily for repositioning. Therefore, DUODERM® paste is not a positioning agent in accordance with the present disclosure, although the remaining compositions listed in Table 5 are effective positioning agents.

Example 2

An experiment was performed to evaluate the mechanical performance, acute in vivo tissue reaction, and handling characteristics of the positioning agents of this disclosure in an acute animal model. Multiple configurations and proce- The study documents the preparation of samples and the implant testing that was performed by a surgeon using various positioning agents of the present disclosure applied to 4"×6" APD MOSAIC™ mesh and 8"×10" APD MOSAIC™ mesh. A 9% solids positioning agent was manufactured according to the formulation outlined in Table 6.

TABLE 6

Exemplary Formulation Tested

| Material | Amount |
|---|---|
| Glycerin | 60.0098 g |
| Sterile water for injection (SWFI) | 1820 ml |
| 12M31P CMC | 119.9774 g |

The % solids of the coating were tested following ASTM D2369-10e1 Standard test method for volatile content of coatings and the results were recorded as 7.83% Solids. The viscosity of the coating formed of the exemplary formulation of Table 6 was tested using an Anton Paar Rheometer, and ranged from 27,200-28,200 Cps when tested at a constant shear rate of 10 $S^{-1}$ and 23° C. Samples of the coating were repackaged into 60 cc syringes. Coating loaded syringes were stored in the refrigerator until the day of the study.

Atrium MOSAIC™ mesh (i.e., an Omega-3 fatty acid coated polypropylene mesh) intended for use in this study was received as a subassembly having been manufactured by manufacturing and processed according to the specific requirements of this experiment. The MOSAIC™ mesh was cut into 4"×6" and 8"×10" APD shapes using an Epilog laser (EQ#06127). Samples were placed on release liners, and placed inside of Foil header pouches, and labeled for traceability. Foil/Tyvek Seals were made and samples were placed in prototype plastic corrugated shipping containers. Samples were sterilized by an Ethylene Oxide (EtO) sterilization technique.

Animal Preparation

Two pigs were used in this study, both of which were 44 kg females. The pigs were anesthetized and prepped for surgery. A total of three ports were inserted into the animals. A laparoscopic irrigator was used to wash the abdominal wall with 0.9% saline solution between samples.

Animal Evaluations of Positioning Agents

Experiment 1—Simulated Clinical Placement of SAM Gel—Size 4"×6" MOSAIC™ Mesh, with External Gel Loading.

TABLE 7

| Experiment 1 Samples | | |
|---|---|---|
| Mesh Lot # | SS00670-085-A3 | 4" × 6" MOSAIC ™ mesh. |
| Positioning Agent Lot # | SS00672-092 | 9% Solids Positioning Agent coating |

The surgeon placed the MOSAIC™ mesh on the bench and dispensed 10 ml of the positioning agent coating on one edge of the rough side of the mesh (i.e., loading of positioning agent on the mesh is external to the test animal). He then rolled the positioning agent coated-mesh with the rough side facing in. The coated mesh was then grasped on one end using laparoscopic graspers and inserted through a 12 mm trocar by the surgeon. The positioning agent-coated mesh device deployed nicely on the viscera. The positioning agent-coated mesh device removed from the viscera very nicely with no evidence of adhered bowel or omentum (i.e., no evidence of trauma to the viscera). The sample positioning agent-coated mesh device adhered very nicely to the abdominal wall. The sample positioning agent-coated mesh device could easily be slid around for repositioning. It could also be removed and replaced for repositioning several times. The surgeon commented that the sample had very good see through clarity. The surgeon reported that the device performed very nicely once it was inside the animal. The surgeon felt that the ability to slide for repositioning was a very good feature. Qualitatively by the above surgical trial, the Experimental 1 Sample constituted a very successful implant.

Experiment 2—Simulated Clinical Placement of SAM Positioning Agent—Size 4"×6" MOSAIC™ Mesh, with Internal Positioning Agent Loading.

TABLE 8

| Experiment 2 Samples | | |
|---|---|---|
| Mesh Lot # | SS00670-085-A4 | 4" × 6" MOSAIC ™ mesh |
| Positioning Agent Lot # | SS00672-092 | 9% Solids Positioning Agent coating |

The mesh sample was inserted dry, through a 12 mm Trocar by the surgeon. The smooth side of the mesh was then placed in contact with the viscera. A 14" section of ⅜" Tygon tubing was attached to the end of a syringe containing the positioning agent. The tubing was then primed with coating so an accurate amount could be dispensed once inside the animal. The tubing was inserted through the 12 mm trocar and 10 ml of the 9% solids coating was randomly distributed on the rough side of the mesh (i.e., loading of the positioning agent on the mesh is performed internally within the test animal). The positioning agent-coated device removed from the viscera very nicely with no evidence of adhered bowel or omentum (i.e., no evidence of injury to the bowel or omentum). The positioning agent-coated mesh sample adhered very nicely to the abdominal wall. The positioning agent-coated mesh sample could easily be slid around for repositioning. It could also be removed and replaced for repositioning several times. The surgeon commented that he felt that the positioning agent-coated mesh of the Experiment 2 sample performed very similar to the Experiment 1 sample that was loaded with the positioning agent outside of the animal. The surgeon commented that the Experiment 2 sample had very good see through clarity. The surgeon thought that the positioning agent-coated mesh device performed very nicely. The surgeon commented on the ability of the positioning agent-coated mesh of the Experiment 2 sample to slide for repositioning or removal of wrinkles, and he reported that this was a very good feature of the positioning agent-coated mesh. Qualitatively by the above surgical trial, the Experimental 2 Sample constituted a very successful implant.

Experiment 3—Simulated Clinical Placement of SAM Positioning Agent—Size 8"×10" MOSAIC™, External Positioning Agent Loading.

TABLE 9

| Experiment 3 Samples | | |
|---|---|---|
| Mesh Lot # | SS00670-085-B1 | 8" × 10" MOSAIC ™ mesh |
| Positioning Agent Lot # | SS00672-092 | 9% Solids Positioning Agent coating |

The surgeon placed the MOSAIC™ mesh on the bench and dispensed 25 ml of the positioning agent coating over the surface of the rough side of the 8"×10" MOSAIC™ mesh. He then rolled the mesh with the rough side facing in. When rolling, the positioning agent could be seen coming through the pores in the MOSAIC™ mesh. The positioning agent-coated mesh was then grasped on one end using laparoscopic graspers, the 12 mm trocar was removed and the positioning agent-coated mesh sample was inserted through the incision site by the surgeon. The positioning agent-coated mesh device remained rolled up on the viscera. The laparoscopic graspers were used to unroll the positioning agent-coated mesh on the viscera. There were no difficulties associated with unrolling the positioning agent-coated mesh on the viscera. The positioning agent-coated mesh device removed from the viscera very nicely with no evidence of adhered bowel or omentum (i.e., no evidence of injury to the bowel or omentum). The positioning agent-coated mesh sample adhered very nicely to the abdominal wall. The positioning agent-coated mesh sample could easily be slid around for repositioning or to remove/reduce wrinkles. It could also be removed and replaced for repositioning several times. The surgeon thought that the positioning agent-coated mesh device performed very nicely. Qualitatively by the above surgical trial, the Experimental 3 Sample constituted a very successful implant.

Experiment 4—Simulated Clinical Placement of SAM Positioning Agent—Size 4"×6" MOSAIC™, External Positioning Agent Loading with Tacking.

TABLE 10

Experiment 4 Samples

| Mesh Lot # | SS00670-085-A2 | 4" × 6" MOSAIC ™ mesh. |
|---|---|---|
| Positioning Agent Lot # | SS00672-092 | 9% Solids Positioning Agent coating |

This animal was also a 44 Kg female pig. The surgeon placed the 4"×6" MOSAIC™ mesh on the bench and dispensed 10 ml of the positioning agent coating on one edge of the rough side of the mesh. He then rolled the positioning agent-coated mesh with the rough side facing in. The positioning agent-coated mesh was then grasped on one end using laparoscopic graspers and inserted through a 12 mm trocar by the surgeon. The positioning agent-coated mesh device deployed nicely on the viscera. The positioning agent-coated mesh device removed from the viscera very nicely with no evidence of adhered bowel or omentum (i.e., no evidence of injury to the bowel or omentum). The positioning agent-coated mesh sample adhered very nicely to the abdominal wall. The positioning agent-coated mesh sample could easily be slid around for repositioning. The surgeon pressed several times on the outside of the abdomen to simulate the use of a tacker and the positioning agent-coated mesh stayed in place very nicely. A Protack tacker from Covidien was used to tack the positioning agent-coated mesh in place. There were no issues related to tacking of this sample. The surgeon observed that it worked very well. The positioning agent-coated mesh held the contour of the abdominal wall very nicely and did not fall off. There were no issues related to the positioning agent-coated mesh sliding or falling down. The use of positioning agents with the MOSAIC™ mesh lends itself very well to tacking. Qualitatively by the above surgical trial, the Experimental 4 Sample constituted a very successful implant.

Figure 7:
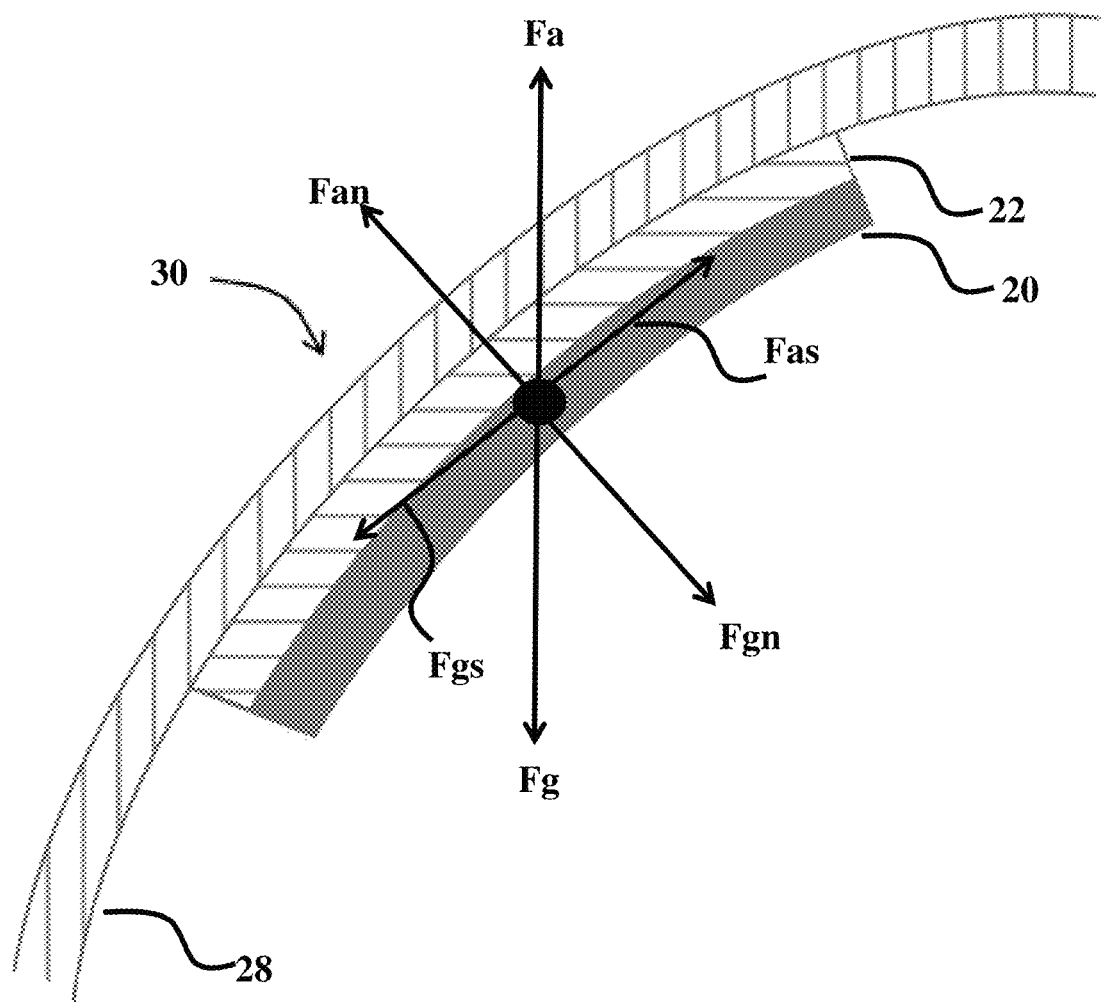
FIG. 7 is a force diagram illustrating the balancing of forces provided by a positioning agent adhering a surgical mesh prosthesis to the wall of a body cavity against gravity.

FIG. 7 illustrates the forces acting on the positioning agent-coated mesh prosthesis as it is held in place against gravity on a tissue surface 28, such as on the contour of the inner abdominal wall, by the positioning agent 22. As shown in FIG. 7, the force of gravity Fg acts on the center of mass of the surgical mesh prosthesis 20 to pull it off the abdominal wall. The positioning agent 22 provides an adhesive force $F_A$ that balances the force of gravity Fg to keep the surgical mesh prosthesis 20 against the inner abdominal wall. The component $Fg_N$ is the component of the force of gravity Fg that is normal to the inner abdominal wall surface, and acts to pull the surgical mesh prosthesis 20 away from the abdominal wall. However, the component $F_{AN}$ of the adhesive force $F_A$ balances force $Fg_N$ to keep the surgical mesh prosthesis 20 from peeling away from the surface of the inner abdominal wall. The component Fgs is the component of the force of gravity Fg that is tangential to the inner abdominal wall surface, and acts to pull the surgical mesh prosthesis 20 down along the abdominal wall. However, the component $F_{AS}$ of the adhesive force $F_A$ balances force Fgs to keep the surgical mesh prosthesis 20 from sliding down the surface of the inner abdominal wall.

Thus, in accordance with a first non-limiting implantable device embodiment of this disclosure, an implantable device is provided that includes: a surgical mesh prosthesis; a positioning agent disposed on a first side of the surgical mesh prosthesis, wherein the positioning agent has an adhesion strength required to maintain the surgical mesh prosthesis temporarily in place, otherwise unsupported, against tissue of a targeted tissue location, wherein the positioning agent exhibits the required adhesion strength in the absence of setting or curing of the positioning agent during implantation of the surgical mesh prosthesis. In accordance with a second non-limiting embodiment of the implantable device, the first non-limiting embodiment is modified so that the positioning agent maintains the surgical mesh prosthesis temporarily in place, otherwise unsupported, against tissue of the targeted tissue location until the surgical mesh prosthesis is permanently fixated in place, against tissue of the targeted tissue location utilizing a fixation device. In accordance with a third non-limiting embodiment of the implantable device, the first and second non-limiting embodiments are further modified so that the positioning agent maintains the surgical mesh prosthesis temporarily in place, otherwise unsupported, against tissue of the targeted tissue location until the surgical mesh prosthesis is permanently fixated in place, against tissue of the targeted tissue location utilizing a fixation device that is not a positioning agent.

In accordance with a fourth non-limiting embodiment of the implantable device, the first, second and third non-limiting embodiments are further modified so that the adhesion strength is characterized by a force of detachment required to pull the implantable device off of the targeted tissue location. In accordance with a fifth non-limiting embodiment of the implantable device, the first, second and third non-limiting embodiments are modified so that the adhesion strength as characterized by a force of detachment required to pull the device off of the targeted tissue location is about 0.10 lbf or less. In accordance with a sixth non-limiting embodiment of the implantable device, the first, second, third, fourth and fifth non-limiting embodiments are further modified so that the viscosity of the positioning agent under shear is sufficient to allow for the mesh prosthesis to slide for repositioning. In accordance with a seventh non-limiting embodiment of the implantable device, the first, second, third, fourth, fifth and sixth non-limiting embodiments are further modified so that the positioning agent enables slidable movement of the prosthesis upon application of a non-gravitational external force without abrading the tissue of the targeted tissue location. In accordance with an eighth non-limiting embodiment of the implantable device, the first, second, third, fourth, fifth, sixth and seventh non-limiting embodiments are further modified so that the positioning agent enables the prosthesis to be peeled away from the targeted tissue location without substantially removing the mesothelium layer from the targeted tissue location. In accordance with a ninth non-limiting embodiment of the implantable device, the first, second, third, fourth, fifth, sixth, seventh and eighth non-limiting embodiments are further modified so that the positioning agent is non-setting.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the embodiments of this disclosure. Details of the structure may vary substantially without departing from the spirit of the subject matter of this disclosure, and exclusive use of all modifications that come within the scope of the appended claims is reserved. Within this specification, embodiments have been described in a way which enables a clear and concise specification to be written, but it is intended and will be appreciated that embodiments may be variously combined or separated without parting from the scope of subject matter disclosed herein. It is intended that the present disclosure shall not be construed as limiting, and that the claimed invention shall be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. An implantable device comprising:
a surgical mesh prosthesis; and
a positioning agent coating one or more surfaces of the surgical mesh prosthesis, wherein the positioning agent is a lubricating non-bonding adhesive possessing an adhesion strength adequate to maintain the surgical mesh prosthesis temporarily in place against gravity, otherwise unsupported, against a target tissue in the absence of setting or curing of the positioning agent, and the positioning agent possesses sufficient lubricity to enable the surgical mesh prosthesis to slide along a surface of the target tissue without substantially traumatizing the target tissue,
wherein the positioning agent comprises a solution, gel or paste that includes water and one or more components selected from the group consisting of glycerin, sodium carboxymethylcellulose, maltrodextrin, hypromellose, carbopol resin, aloe vera, collagen and xantham gum, and wherein the lubricity of the positioning agent is characterized by a dynamic viscosity of the positioning agent that comprises a first viscosity, when tested at 0.1 $S^{-1}$ and 23° C., between about 150 Cps and 26,000,000 Cps, and a second viscosity, when tested at 9.77 $S^{-1}$ and 23° C., that is between about 50 Cps and 2,530,000 Cps.

2. The implantable device according to claim 1, wherein the positioning agent is a hydrogel comprising mostly water, and includes glycerin, or sodium carboxymethylcellulose, or both glycerin and sodium carboxymethylcellulose.

3. The implantable device according to claim 2, wherein the adhesive strength of the positioning agent includes a substantially non-zero force of detachment with a maximum force of detachment of less than about 0.1 lbf by lap shear test performed at constant speed of 45 in/min.

4. The implantable device according to claim 1, wherein the positioning agent includes a solvent.

5. The implantable device according to claim 4, wherein the adhesive strength of the positioning agent includes a substantially non-zero force of detachment with a maximum force of detachment of less than about 0.1 lbf by lap shear test performed at constant speed of 45 in/min.

6. The implantable device according to claim 1, wherein the positioning agent includes a polymer.

7. The implantable device according to claim 6, wherein the adhesive strength of the positioning agent includes a substantially non-zero force of detachment with a maximum force of detachment of less than about 0.1 lbf by lap shear test performed at constant speed of 45 in/min.

8. A kit comprising:
a surgical mesh prosthesis; and
a non-setting positioning agent, wherein the positioning agent has an adhesion strength adequate to maintain the surgical mesh prosthesis temporarily in place against gravity, otherwise unsupported, against tissue of a targeted tissue location until the surgical mesh prosthesis is secured permanently in place utilizing a fixation mechanism, wherein the surgical mesh prosthesis and the positioning agent are packaged separately, and wherein when the positioning agent is used to coat one or more sides of the surgical mesh prosthesis, the result is the implantable device according to claim 1.

9. An implantable device comprising:
a surgical mesh prosthesis; and
a positioning agent coating one or more surfaces of the surgical mesh prosthesis, wherein the positioning agent is a lubricating non-bonding adhesive possessing an adhesion strength adequate to maintain the surgical mesh prosthesis temporarily in place against gravity, otherwise unsupported, against a target tissue in the absence of setting or curing of the positioning agent, and the positioning agent possesses sufficient lubricity to enable the surgical mesh prosthesis to slide along a surface of the target tissue without substantially traumatizing the target tissue, wherein the positioning agent comprises a solution, gel or paste that includes water and one or more components selected from the group consisting of glycerin, sodium carboxymethylcellulose, maltrodextrin, hypromellose, carbopol resin, aloe vera, collagen and xantham gum, and wherein the lubricity of the positioning agent is characterized by a dynamic viscosity of the positioning agent that comprises a first viscosity, when tested at 0.1 $S^{-1}$ and 23° C., between about 150 Cps and 26,000,000 Cps, and a second viscosity, when tested at 9.77 $S^{-1}$ and 23° C., that is between about 50 Cps and 2,530,000 Cps, and wherein the adhesive strength of the positioning agent includes a substantially non-zero force of detachment with a maximum force of detachment of less than about 0.1 lbf by lap shear test performed at constant speed of 19 mm/s for a 1" by 1" portion of the surgical mesh prosthesis.

* * * * *